US006911445B2

(12) United States Patent
Evrard et al.

(10) Patent No.: US 6,911,445 B2
(45) Date of Patent: Jun. 28, 2005

(54) ANTIDEPRESSANT CYCLOALKYLAMINE DERIVATIVES OF HETEROCYCLE-FUSED BENZODIOXANS

(75) Inventors: Deborah Ann Evrard, Hamilton Square, NJ (US); Gary Paul Stack, Ambler, PA (US); Uresh Shantilal Shah, Cranbury, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/659,174

(22) Filed: Sep. 10, 2003

(65) Prior Publication Data

US 2004/0171667 A1 Sep. 2, 2004

Related U.S. Application Data

(60) Provisional application No. 60/410,072, filed on Sep. 12, 2002.

(51) Int. Cl.[7] .................... A61K 31/495; C07D 241/46; C07D 491/08; C07D 235/02
(52) U.S. Cl. ...................... 514/250; 514/291; 514/267; 514/375; 514/394; 514/411; 544/345; 544/250; 546/90; 548/218; 548/430; 548/302.1
(58) Field of Search ................................ 514/250, 291, 514/267, 375, 394, 411; 544/345, 250; 546/90; 548/218, 430, 302.1

(56) References Cited

U.S. PATENT DOCUMENTS 6,162,803 A * 12/2000 Mewshaw et al. ....... 514/230.5

FOREIGN PATENT DOCUMENTS

| WO | 97/17343 A1 | 5/1997 |
|---|---|---|
| WO | 98/29415 A1 | 7/1998 |
| WO | 98/40386 A1 | 9/1998 |
| WO | WO 99/51592 | * 10/1999 |
| WO | 02/072587 A1 | 9/2002 |
| WO | 02/088135 A1 | 11/2002 |

OTHER PUBLICATIONS

Krogsgaard–Larsen, et al. (Eds.), "Design and Application of Prodrugs," *Texbook of Drug Design and Development*, 1991, Chap. 5, 113–191.
Lazareno, S., et al., "Pharmacological characterization of acetylcholine–stimulated [$^3$S]–GTPγS binding mediated by human muscarinic m1–m4 receptors: antagonist studies," *Br. J. Pharmacol.*, 1993, 109, 1120–1127.
Ostrowski, S., "A synthesis of fused pyrimidine mono–n–oxides," Heterocycles, 1996, 43(2), p. 389–396.
Perez, V., et al., "Randomised, double–blind, placebo–controlled trial of pindolol in combination with fluoxetine antidepressant treatment," *The Lancet*,m May 31, 1997, 349, 1594–1597.

Tome, M.B., et al., "Serotonergic autoreceptor blocade in the reduction of antidepressant latency: personality variables and response to paroxetine and pindolol," *J. Affect Disord*, 1997, 44, 101–109.
Tome, M.B., et al., "Paroxetine and pindolol: a randomized trial of serotonergic antoreceptor blockade in the reduction of antidepressant latency," *Int. Clin. Psychopharmacol*, 1997, 12, 81–89.
Wilen, S.H., "Tables of Resolving Agents and Optical Resolutions," *Univ. of Notre Dame Press, Notre Dame, IN*, E.L. Eliel (Ed.), 1972, p. 268–298.
Wilen, S.H., et al., "Strategies in optical resolutions," *Tetrahedron*, 1977, 33, 2725–2736.
Artigas, F., et al., "Pindolol induces a rapid improvement of depressed patients treated with serotonin reuptake inhibitors," *Arch Gen Psychiatry*, Mar. 1994, 51, 248–251.
Blier, P., et al., "Effectiveness of pindolol with selected antidepressant drugs in the treatment of major depression," *J. of Clinical Psychopharmacology*, 1995, 15(3), 217–222.
Bundgaard, H., "Means to enhance penetration; Prodrugs as a means to improve the delivery of peptide drugs," Advanced *Drug Deliver Reviews*, 1992, 8, 1–38.
Cheetham, S.C., et al., "[$^3$H]paroxetine binding in rat frontal cortex strongly correlates with [$^3$H]5–HT uptake: effect of administration of various antidepressant treatments," *Neuropharmacol.*, 1993, 32(8), 737–743.
Hall, M.D., et al., "[$^3$H] 8–hydroxy–2–(Di–n–propylamino)tetralin binding to pre– and postsynaptic 5–hydroxytryptamine sites in various regions of the rat brain," *J. Neurochem.*, 1985, 44, 1685–1696.

* cited by examiner

Primary Examiner—D. Margaret Seaman
(74) Attorney, Agent, or Firm—Woodcock Washburn LLP

(57) ABSTRACT

Compounds of the formula:

I

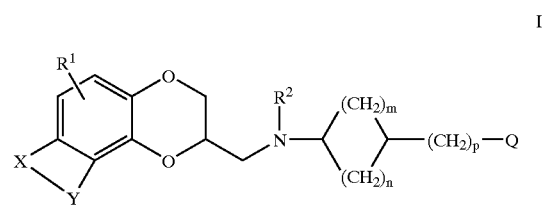

are useful for the treatment of depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive-compulsive disorder, social anxiety disorder, generalized anxiety disorder, obesity, eating disorders, vasomotor flushing, cocaine and alcohol addiction, sexual dysfunction and related illnesses.

30 Claims, No Drawings

ANTIDEPRESSANT CYCLOALKYLAMINE DERIVATIVES OF HETEROCYCLE-FUSED BENZODIOXANS

CROSS-REFERENCE TO RELATED APPLICATIONS

This application is a continuation-in-part application of U.S. application Ser. No. 60/410,072, filed Sep. 12, 2002, the disclosure of which is incorporated herein by reference in its entirety.

FIELD OF THE INVENTION

This invention relates to antidepressant cycloalkylamine derivatives of heterocycle-fused benzodioxans, to processes for preparing them, methods of using them and to pharmaceutical compositions containing them.

BACKGROUND OF THE INVENTION

Major depression is a serious health problem affecting more than 5% of the population, with a lifetime prevalence of 15–20%.

Selective serotonin reuptake inhibitors have produced success in treating depression and related illnesses and have become among the most prescribed drugs. They nonetheless have a slow onset of action, often taking several weeks to produce their full therapeutic effect. Furthermore, they are effective in less than two-thirds of patients.

Serotonin selective reuptake inhibitors (SSRIs) are well known for the treatment of depression and other conditions. SSRIs work by blocking the neuronal reuptake of serotonin, thereby increasing the concentration of serotonin in the synaptic space, and thus increasing the activation of postsynaptic serotonin receptors.

However, although a single dose of an SSRI can inhibit the neuronal serotonin transporter which would be expected to increase synaptic serotonin, long-term treatment is required before clinical improvement is achieved.

It has been suggested that the SSRIs increase the serotonin levels in the vicinity of the serotonergic cell bodies and that the excess serotonin activates somatodendritic autoreceptors, $5HT_{1A}$ receptors, causing a decrease in serotonin release in major forebrain areas. This negative feedback limits the increment of synaptic serotonin that can be induced by antidepressants.

A $5HT_{1A}$ antagonist would limit the negative feedback and should improve the efficacy of the serotonin reuptake mechanism (Perez, V., et al., *The Lancet*, 349:1594–1597 (1997)). Such a combination therapy would be expected to speed up the effect of the serotonin reuptake inhibitor.

Thus, it is highly desirable to provide improved compounds which both inhibit serotonin reuptake and which are antagonists of the $5HT_{1A}$ receptor.

DESCRIPTION OF THE INVENTION

In accordance with this invention, there is provided a group of novel compounds of the formula:

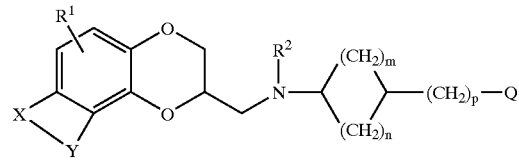

wherein $R^1$ is hydrogen, hydroxy, halo, cyano, carboxamido, carboalkoxy of 2 to 6 carbon atoms, trifluoromethyl, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen or alkyl of 1 to 6 carbons;

the group X—Y is —N=C($R^3$)—C($R^4$)=N—, —N=C($R^3$)—C($R^5$)=CH—, —N=C($R^3$)—N=CH—, —N=C($R^3$)—O—, —NH—C($R^6$)=N— or —NH—C($R^7$)=CH—;

$R^3$ and $R^4$ are, independently, hydrogen, halo, amino, mono- or di-alkylamino in which each alkyl group has 1 to 6 carbon atoms or alkyl of 1 to 6 carbon atoms;

$R^5$ is hydrogen or alkyl of 1 to 6 carbon atoms;

$R^6$ is hydrogen, halo, trifluoromethyl, pentafluoroethyl, amino, mono- or di-alkylamino in which each alkyl group has 1 to 6 carbon atoms or alkyl of 1 to 6 carbon atoms;

$R^7$ is hydrogen, halo, trifluoromethyl, pentafluoroethyl or alkyl of 1 to 6 carbon atoms;

m is 1 to 3;

n is 1 to 2;

p is 0 to 3;

Q is a heteroaryl moiety selected from the following:

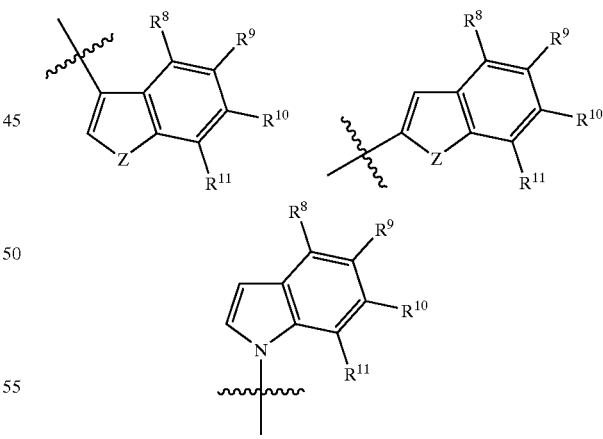

wherein Z is $NR^{12}$, S, or O;

$R^8$, $R^9$, $R^{10}$, and $R^{11}$ are, independently, hydrogen, hydroxy, halo, cyano, carboxamido, carboalkoxy of 2 to 6 carbon atoms, trifluoromethyl, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; and $R^{12}$ is hydrogen or alkyl of 1 to 6 carbon atoms;

or pharmaceutically acceptable salts thereof.

$R^1$ is preferably hydrogen, halo, cyano, trifluoromethyl, alkyl of 1 to 6 carbon atoms or alkoxy of 1 to 6 carbon atoms. More preferably, $R^1$ is hydrogen, halo or alkoxy of 1 to 6 carbon atoms. In still more preferred embodiments of the present invention, $R^1$ is hydrogen.

$R^2$ and $R^5$ are preferably independently selected from hydrogen or alkyl of 1 to 3 carbon atoms.

Preferably, the group X—Y is —N=C($R^3$)—C($R^5$)=CH— or —N=C($R^3$)—O—.

$R^3$ and $R^4$ are preferably independently selected from hydrogen, amino or alkyl of 1 to 6 carbon atoms. More preferably, $R^3$ and $R^4$ are independently hydrogen or alkyl of 1 to 3 carbon atoms.

$R^6$ and $R^7$ are preferably independently selected from hydrogen, trifluoromethyl, pentafluoroethyl or alkyl of 1 to 6 carbon atoms. More preferably, $R^6$ and $R^7$ are independently hydrogen, trifluoromethyl or alkyl of 1 to 3 carbon atoms.

$R^8$, $R^9$, $R^{10}$, and $R^{11}$ are preferably independently selected from hydrogen, hydroxy, halo, cyano, carboxamido, alkyl of 1 to 6 carbon atoms, or alkoxy of 1 to 6 carbon atoms. In still more preferred embodiments of the present $R^8$, $R^9$, $R^{10}$, and $R^{11}$ are preferably independently selected from hydrogen, cyano or halogen.

Z is preferably $NR^{12}$. When Z is $NR^{12}$, $R^{12}$ is preferably hydrogen or alkyl of 1 to 3 carbon atoms.

The integers m and n are independently preferably 1 or 2. More preferably, m is 1 and n is 2.

The integer p is preferably 0 or 1. More preferably, p is 0.

Preferably, Q is a heteroaryl moiety of the formula

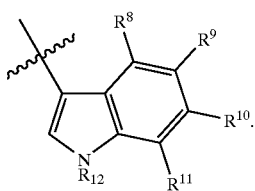

In other preferred embodiments of the invention is provided compounds of Formula Ia Ia

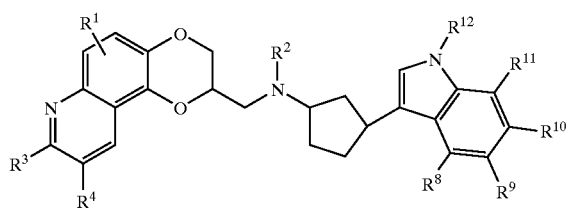

wherein $R^1$, $R^2$, $R^3$, $R^4$, $R^8$, $R^9$, $R^{10}$, $R^{11}$, and $R^{12}$ are as described above.

In still other preferred embodiments of the invention is provided compounds of Formula Ib Ib

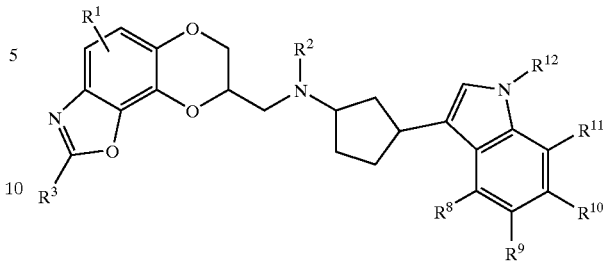

wherein $R^1$, $R^2$, $R^3$, $R^8$, $R^9$, $R^{10}$, $R^{11}$, and $R^{12}$ are as described above.

This invention relates to both the R and S stereoisomers of the benzodioxan methylamines as well as to mixtures of the R and S stereoisomers. Throughout this application, the name of the product of this invention, where the absolute configuration of the compounds of the invention is not indicated, is intended to embrace the individual R and S enantiomers as well as mixtures of the two. In some embodiments of the present invention the S enantiomer is preferred. For certain of the compounds of the invention (i.e., X—Y forms an imidazole), tautomeric forms may exist. This application thus encompasses all tautomeric forms of compounds of the present invention.

It will be recognized that the substituents on di-substituted cycloalkyl rings may be arranged with cis or trans relative stereochemistry. It will be further recognized that when n is 1, the cyclopentyl moiety of the present invention contains two asymmetric carbon atoms. Thus, in addition to cis and trans isomers, additional stereoisomers are possible for the cyclopentylamine moiety. This application thus encompasses all stereoisomers, individually or as mixtures, of the cycloalkylamine moiety. Furthermore, this application relates to all possible diastereomers, individually or as mixtures, of the compounds of the present invention.

Where a single stereoisomer is preferred, it may, in some embodiments be provided substantially free of the corresponding enantiomer or diastereomers. Thus, a single stereoisomer substantially free of the corresponding enantiomer or diastereomers refers to a compound which is isolated or separated via separation techniques or prepared free of the corresponding enantiomer or diastereomers. "Substantially free," as used herein, means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures or diastereomeric mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

"Alkyl," as used herein, refers to an aliphatic hydrocarbon chain and includes straight and branched chains such as methyl, ethyl, n-propyl, isopropyl, n-butyl, isobutyl, secbutyl, t-butyl, n-pentyl, isopentyl, neo-pentyl, n-hexyl, and isohexyl. "Lower alkyl" refers to alkyl having 1 to 3 carbon atoms.

"Alkanamido," as used herein, refers to the group R—C(=O)—NH— where R is an alkyl group of 1 to 5 carbon atoms.

"Alkanoyloxy," as used herein, refers to the group R—C(=O)—O— where R is an alkyl group of 1 to 5 carbon atoms.

"Alkanesulfonamido," as used herein, refers to the group R—S(O)$_2$—NH—where R is an alkyl group of 1 to 6 carbon atoms.

"Alkoxy," as used herein, refers to the group R—O— where R is an alkyl group of 1 to 6 carbon atoms.

"Carboxamido," as used herein, refers to the group NH$_2$—C(=O)—.

"Carboalkoxy," as used herein refers to the group R—O—C(=O)— where R is an alkyl group of 1 to 5 carbon atoms.

"Halogen" (or "halo"), as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific examples of compounds of Formula I are:

N-[(cis)-3-(1H-indol-3-yl)cyclopentyl]-N-{[(2S)-8-methyl-2,3-dihydro[1,4]dioxino[2,3-f]quinolin-2-yl]methyl}amine;

N-[(trans)-3-(1H-indol-3-yl)cyclopentyl]-N-{[(2S)-8-methyl-2,3-dihydro[1,4]dioxino[2,3-f]quinolin-2-yl]methyl}amine;

N-[(cis)-3-(5-fluoro-1H-indol-3-yl)cyclopentyl]-N-{[(2S)-8-methyl-2,3-dihydro[1,4]dioxino[2,3-f]quinolin-2-yl]methyl}amine;

N-[(1R,3S)-3-(5-fluoro-1H-indol-3-yl)cyclopentyl]-N-{[(2S)-8-methyl-2,3-dihydro[1,4]dioxino[2,3-f]quinolin-2-yl]methyl}amine;

N-[(1S,3R)-3-(5-fluoro-1H-indol-3-yl)cyclopentyl]-N-{[(2S)-8-methyl-2,3-dihydro[1,4]dioxino[2,3-f]quinolin-2-yl]methyl}amine;

N-[(trans)-3-(5-fluoro-1H-indol-3-yl)cyclopentyl]-N-{[(2S)-8-methyl-2,3-dihydro[1,4]dioxino[2,3-f]quinolin-2-yl]methyl}amine;

N-[(1R,3R)-3-(5-fluoro-1H-indol-3-yl)cyclopentyl]-N-{[(2S)-8-methyl-2,3-dihydro[1,4]dioxino[2,3-f]quinolin-2-yl]methyl}amine;

N-[(1S,3S)-3-(5-fluoro-1H-indol-3-yl)cyclopentyl]-N-{[(2S)-8-methyl-2,3-dihydro[1,4]dioxino[2,3-f)quinolin-2-yl]methyl}amine;

N-[(cis)-3-(5-fluoro-1H-indol-3-yl)cyclopentyl]-N-methyl-N-{[(2S)-8-methyl-2,3-dihydro[1,4]dioxino[2,3-f]quinolin-2-yl]methyl}amine;

N-[(cis)-3-(5-fluoro-1-methyl-1H-indol-3-yl)cyclopentyl]-N-{[(2S)-8-methyl-2,3-dihydro[1,4]dioxino[2,3-f]quinolin-2-yl]methyl}amine;

N-[(1R,3S)-3-(5-fluoro-1-methyl-1H-indol-3-yl)cyclopentyl]-N-{[(2S)-8-methyl -dihydro[1,4]dioxino[2,3-f]quinolin-2-yl]methyl}amine;

N-[(1S,3R)-3-(5-fluoro-1-methyl-1H-indol-3-yl)cyclopentyl]-N-{[(2S)-8-methyl -dihydro[1,4]dioxino[2,3-f]quinolin-2-yl]methyl}amine;

N-[(trans)-3-(5-fluoro-1-methyl-1H-indol-3-yl)cyclopentyl]-N-{[(2S)-8-methyl-2,3-dihyro[1,4]dioxino[2,3-f]quinolin-2-yl]methyl}amine;

N-[(cis)-4-(5-fluoro-1H-indol-3-yl)cyclohexyl]-N-{[(2S)-8-methyl-2,3-dihydro[1,4]dioxino[2,3-f]quinolin-2-yl]methyl}amine;

N-[(trans)-4-(5-fluoro-1H-indol-3-yl)cyclohexyl]-N-{[(2S)-8-methyl-2,3-dihydro[1,4]dioxino[2,3-f]quinolin-2-yl]methyl}amine;

N-[(trans)-3-(5-Fluoro-1H-indol-3-yl)cyclopentyl]-N-{[(8S)-2-methyl-7,8-dihydro[1,4]dioxino[2,3-g][1,3]benzoxazol-8-yl]methyl}amine;

N-[(cis)-3-(5-Fluoro-1H-indol-3-yl)cyclopentyl]-N-{[(8S)-2-methyl-7,8-dihydro[1,4]dioxino[2,3-g][1,3]benzoxazol-8-yl]methyl}amine;

N-[(cis)-4-(5-fluoro-1H-indol-3-yl)cyclohexyl]-N-{[(8S)-2-methyl-7,8-dihydro[1,4]dioxino[2,3-g][1,3]benzoxazol-8-yl]methyl}amine;

N-[(1R*,3S*)-3-(5-fluoro-1H-indol-3-yl)cyclopentyl)-N-methyl-N-{[(2S)-8-methyl-2,3-dihydro[1,4]-dioxino[2,3-f]quinolin-2-yl]methyl}amine;

and pharmaceutically acceptable salts thereof.

In another aspect, the invention relates to a method of treating a subject suffering from a condition selected from depression, anxiety, panic disorder, post-traumatic stress disorder, premenstrual dysphoric disorder, attention deficit disorder, obsessive compulsive disorder, social anxiety disorder, generalized anxiety disorder, obesity, eating disorders such as anorexia nervosa and bulimia nervosa, vasomotor flushing, cocaine and alcohol addiction, and sexual dysfunction which comprises providing to the subject suffering from said condition, a therapeutically effective amount of a compound of the invention or a pharmaceutically acceptable salt thereof.

In a further aspect, the invention relates to a pharmaceutical composition comprising an effective amount of a compound of the invention or a pharmaceutically acceptable salt thereof and a pharmaceutically acceptable carrier or excipient.

In a further aspect, the invention relates to a compound of the invention or a pharmaceutically acceptable salt thereof for use as a medicament.

In a still further aspect, the invention relates to the use of a compound of the invention or a pharmaceutically acceptable salt thereof in the preparation of a medicament for the treatment of depression, anxiety, panic disorder, post-traumatic stress disorder, premenstrual dysphoric disorder, attention deficit disorder, obsessive compulsive disorder, social anxiety disorder, generalized anxiety disorder, obesity, eating disorders such as anorexia nervosa and bulimia nervosa, vasomotor flushing, cocaine and alcohol addiction, and sexual dysfunction.

Compounds of the present invention are suitably prepared in accordance with the following general description and specific examples. Variables used are as defined for Formula I, unless otherwise noted. Specifically (Scheme 1), the appropriately substituted cycloalkylamine is combined with a suitably substituted benzodioxan methyltosylate in a solvent such as dimethyl sulfoxide and heated to a temperature of 70–100° C. for several hours as illustrated below.

Scheme 1

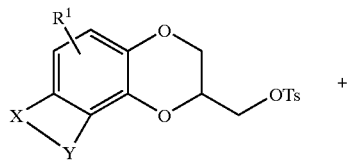

-continued

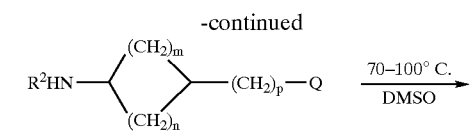

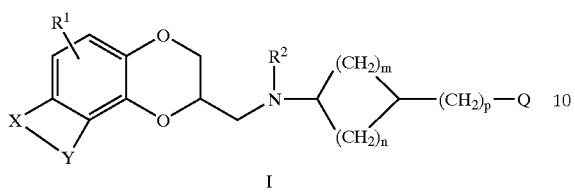

Alternatively compounds of the present invention may be prepared as shown in Scheme 2 below. Specifically, a suitably substituted benzodioxan methyltosylate or bromide is converted the corresponding azide by reaction with sodium or potassium azide in an appropriate solvent such as dimethylformamide or dimethylsulfoxide. The azide is then conveniently reduced to the primary amine by methods known to those skilled in the art, such as hydrogenation over palladium on carbon. The amine is then combined with an appropriately substituted cycloalkanone in the presence of a reducing agent such as sodium triacetoxyborohydride or sodium cyanoborohydride to give the compounds of the invention wherein $R^2$ is hydrogen.

Scheme 2

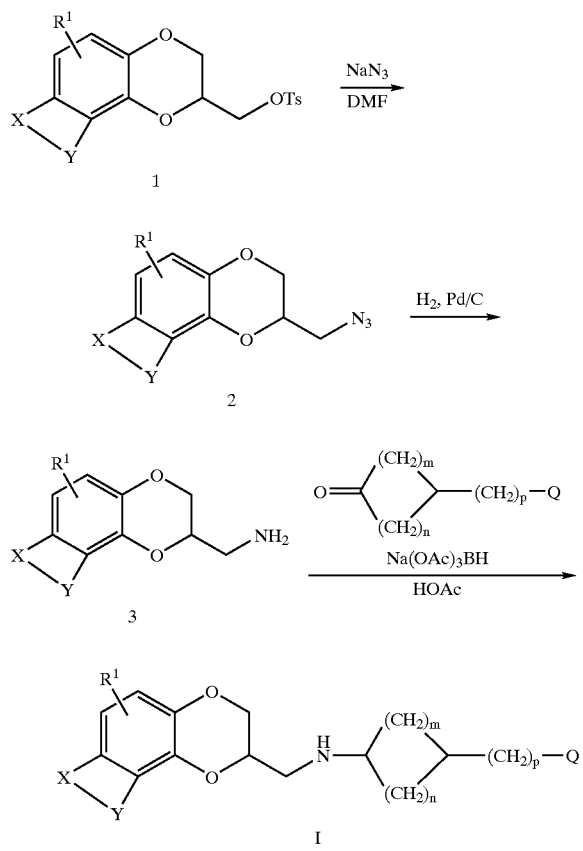

Compounds in which $R^2$ is alkyl may be prepared as in Scheme 1 above, or may be alternatively prepared from compounds of Formula I in which $R^2$ is hydrogen by reaction with a suitable aldehyde or ketone in the presence of a reducing agent such as sodium triacetoxy borohydride or sodium cyanoborohydride, as shown in Scheme 3.

Scheme 3

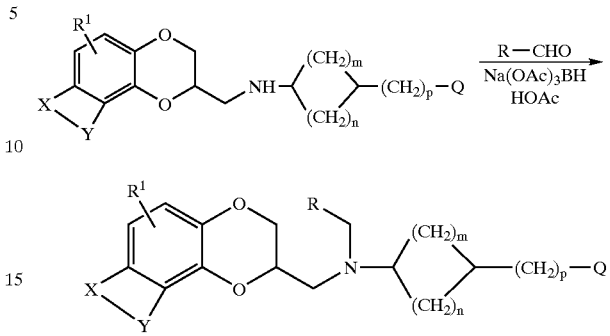

The 2,3-dihydro-1,4-dioxino[2,3-f]quinolin-2-ylmethyltosylates (11) in which $R^3$ is H can be prepared as illustrated in Scheme 4 below. Specifically, the appropriately substituted nitroguaiacol (5) is alkylated with allyl bromide in the presence of a suitable base such as sodium hydride to produce (6) and then demethylated by a reagent such as sodium hydroxide. The resulting 4-nitro-2-allyloxyphenol (7) is then alkylated with glycidyl Scheme 4

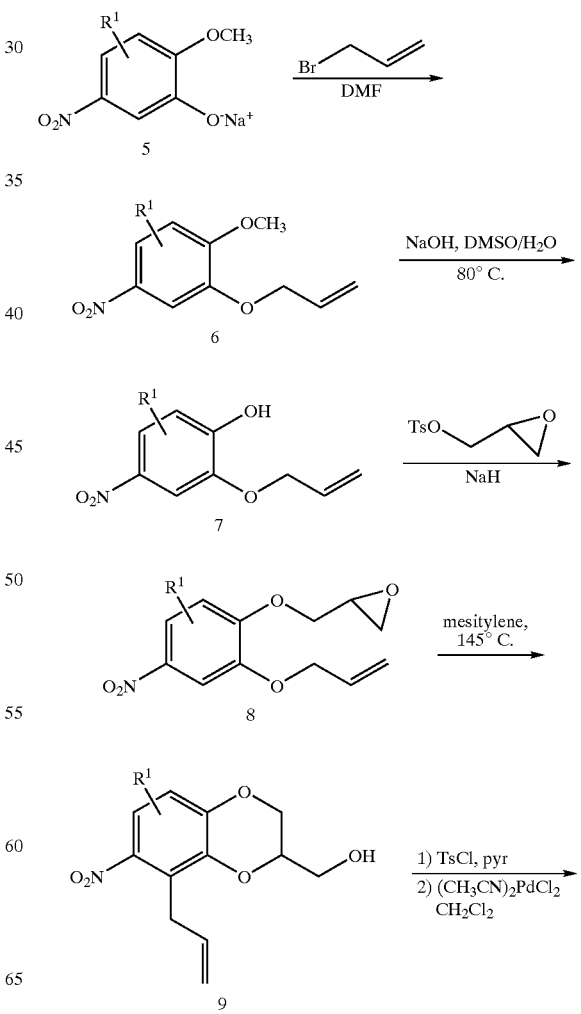

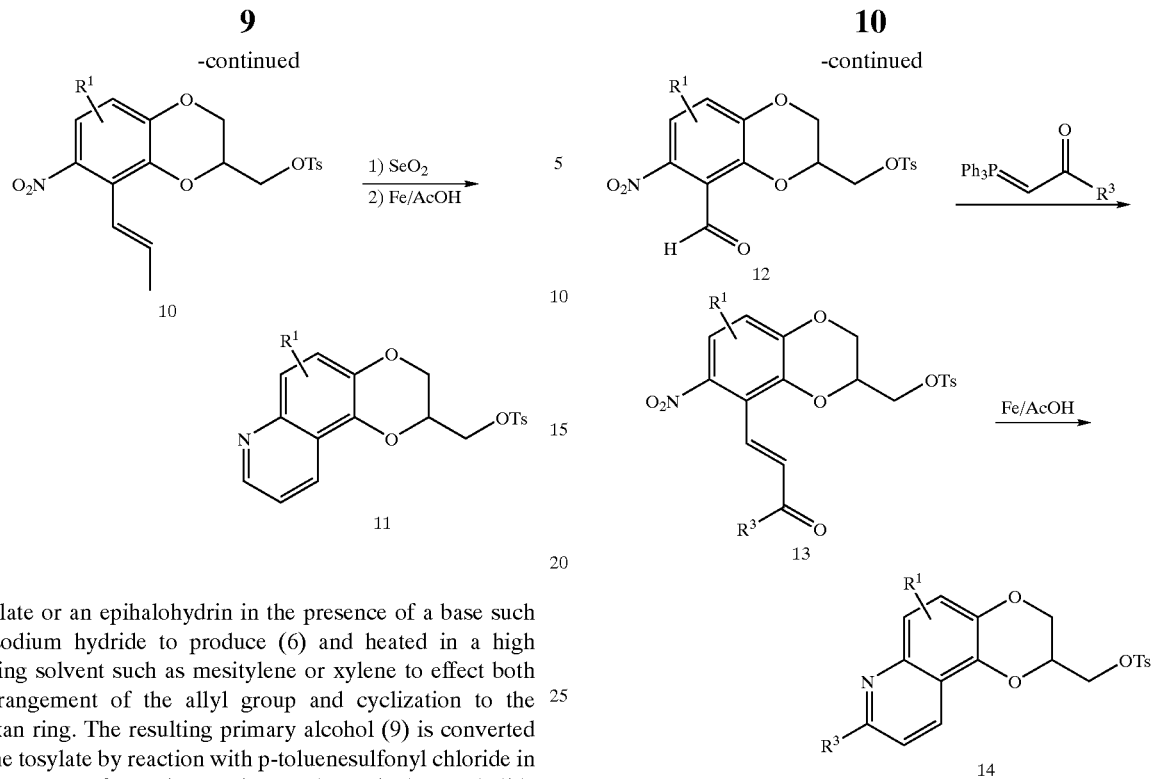

tosylate or an epihalohydrin in the presence of a base such as sodium hydride to produce (6) and heated in a high boiling solvent such as mesitylene or xylene to effect both rearrangement of the allyl group and cyclization to the dioxan ring. The resulting primary alcohol (9) is converted to the tosylate by reaction with p-toluenesulfonyl chloride in the presence of a tertiary amine or alternatively to a halide by reaction with carbon tetrabromide or carbon tetrachloride in combination with triphenylphosphine. The allyl side chain is then isomerized by treatment with catalytic bis-acetonitrile palladium (II) chloride in refluxing methylene chloride or benzene to produce (10). Allylic oxidation with selenium dioxide in refluxing dioxane/water gives the o-nitrocinnamaldehyde, which upon reduction with iron in acetic acid cyclizes to the 2,3-dihydro-1,4-dioxino[2,3-f] quinoline-2-methyl-tosylate or halide (11).

The 2,3-dihydro-1,4-dioxino[2,3-f]quinolin-2-ylmethyltosylates (14) in which $R^3$ is alkyl may be prepared from the nitro olefin described above in the manner described in Scheme 5. The rearranged olefin (10) is treated sequentially with ozone and a tertiary amine or with osmium tetroxide and sodium periodate to give the o-nitrobenzaldehyde (12). Condensation with the appropriate triphenylphosphoranylidene ketone under Wittig conditions gives the o-nitrostyryl ketone (13), which upon reduction by iron in acetic acid, cyclizes to the corresponding 2,3-dihydro-1,4-dioxino[2,3-f]-quinoline-2-methyltosylate (14). Replacement of the tosylate with the appropriately substituted cycloalkylamine as above gives the title compounds of the invention.

Substitution of trimethyl phosphonoacetate for the triphenylphosphoranylidene ketone in the Wittig procedure above, followed by reduction of the nitro group with tin (II) chloride and cyclization in acid gives the compounds of the invention in which $R^3$ is hydroxy. Alkylation of this hydroxy derivative by a suitable alkyl halide or tosylate in the presence of base gives the compounds of the invention in which $R^3$ is alkoxy. Treatment of the hydroxy derivative with an inorganic acid chloride such as phosphoryl chloride or bromide gives the compounds of the invention in which $R^3$ is halo. Substitution of diethyl cyanomethylphosphonate for the triphenyl-phosphoranylidene ketone in the Wittig procedure above, followed by reduction of the nitro group with tin (II) chloride and cyclization in acid gives the compounds of the invention in which $R^3$ is amino.

The o-nitrobenzaldehyde (12) used in the Wittig chemistry described in Scheme 5 may be alternatively prepared as shown in Scheme 6. The appropriate mono-allylated catechol (15) is elaborated with glycidyl tosylate as described above to produce (16) and rearranged in refluxing mesitylene. Cyclization to the benzodioxan methanol is Scheme 5

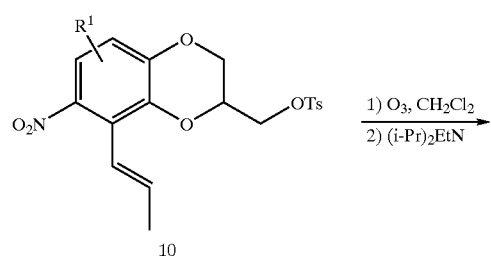

Scheme 6

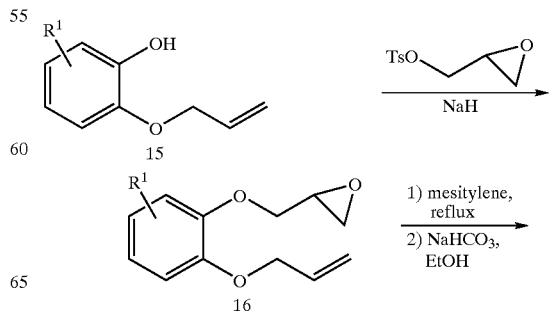

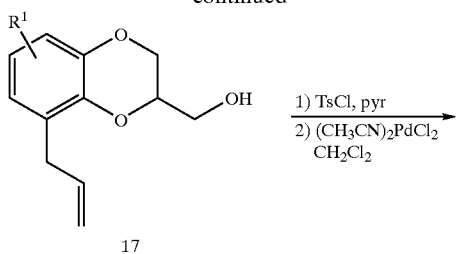

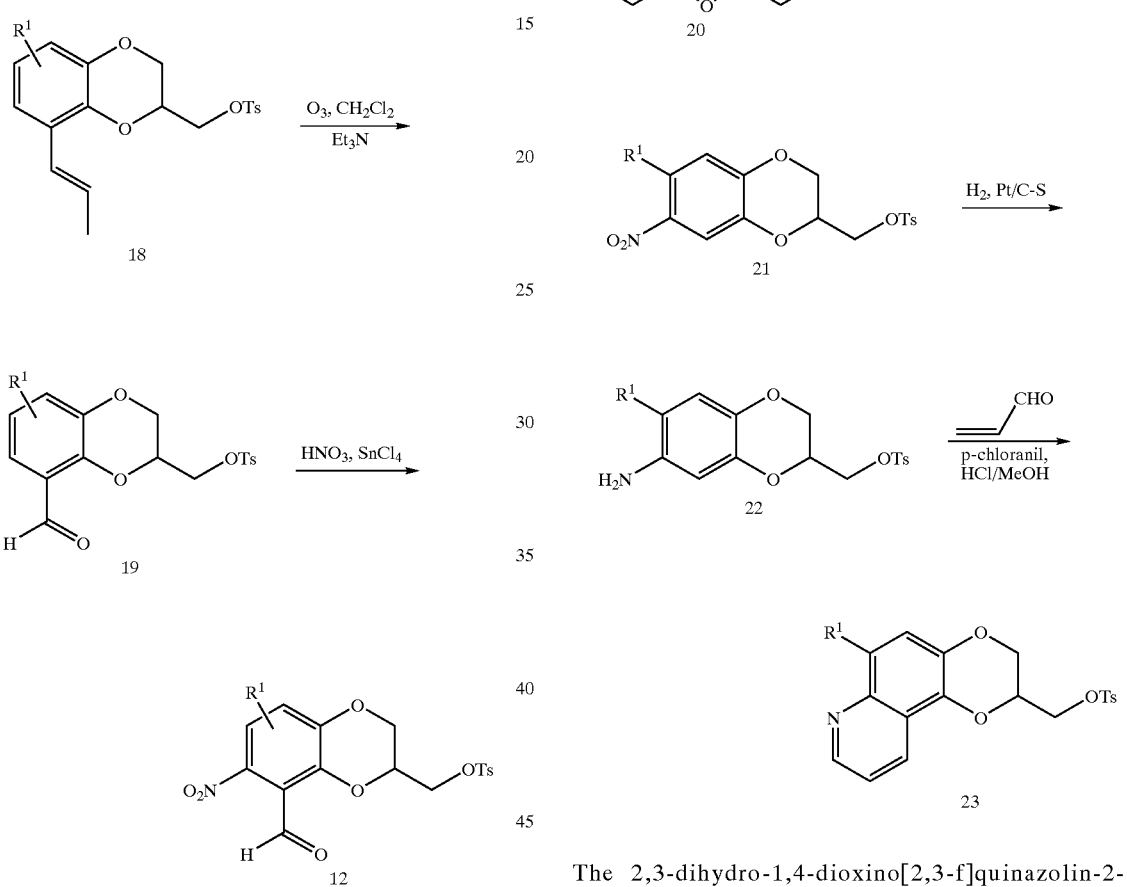

effected by treatment with sodium bicarbonate in ethanol and the alcohol (17) is converted to the tosylate or halide. After rearrangement of the double bond by treatment with catalytic bis-acetonitrile palladium chloride in refluxing methylene chloride to produce 18 and cleavage with ozone or osmium tetroxide/sodium periodate as described above, the resulting aldehyde (19) is regioselectively nitrated with a combination of nitric acid and tin (IV) chloride to produce (12).

Compounds of the invention in which $R^1$ is attached to position 6 of the 2,3-dihydro-1,4-dioxino[2,3-f]quinoline may be alternatively prepared by a variation of the Skraup quinoline synthesis according to Scheme 7. The appropriately substituted benzodioxan methyltosylate (20) is nitrated under standard conditions with nitric acid in a solvent such as dichloroethane and the resulting nitro compound (21) reduced by treatment with hydrogen in the presence of a catalyst such as platinum on sulfide carbon. Treatment of the resulting aniline (22) with acrolein in the presence of hydrogen chloride and an oxidant such as p-chloranil or naphthoquinone gives the corresponding 2,3-dihydro-1,4-dioxino(2,3-f)quinoline (23). Replacement of the tosylate with the appropriately substituted cycloalkylamine as above gives the title compounds of the invention.

The 2,3-dihydro-1,4-dioxino[2,3-f]quinazolin-2-ylmethylamines of the invention are prepared as illustrated below (Scheme 8). The o-nitrobenzaldehyde (12) described above is converted to the oxime (24) by treatment with hydroxylamine hydrochloride in the presence of a suitable base such as sodium acetate and the nitro group reduced to the amine by hydrogenation over palladium on carbon. Cyclization to the quinazoline N-oxide is effected by treatment at reflux with the appropriate ortho ester according to the method of Ostrowski (Heterocycles, vol. 43, No. 2, p. 389, 1996). The quinazoline N-oxide may be reduced to the quinazoline (25) by a suitable reducing agent such as hydrogen over Raney-nickel. Alternatively, an extended period of reflux in the ortho ester gives the reduced quinazoline directly via a disproportionation reaction and the 2,3-dihydro-1,4-dioxino(2,3-f)quinazoline-2-methyltosylate or halide may be isolated by column chromatography. Replacement of the tosylate or halide with the appropriately substituted cycloalkylamine in some high boiling solvent such as dimethyl sulfoxide gives the title compounds of the invention.

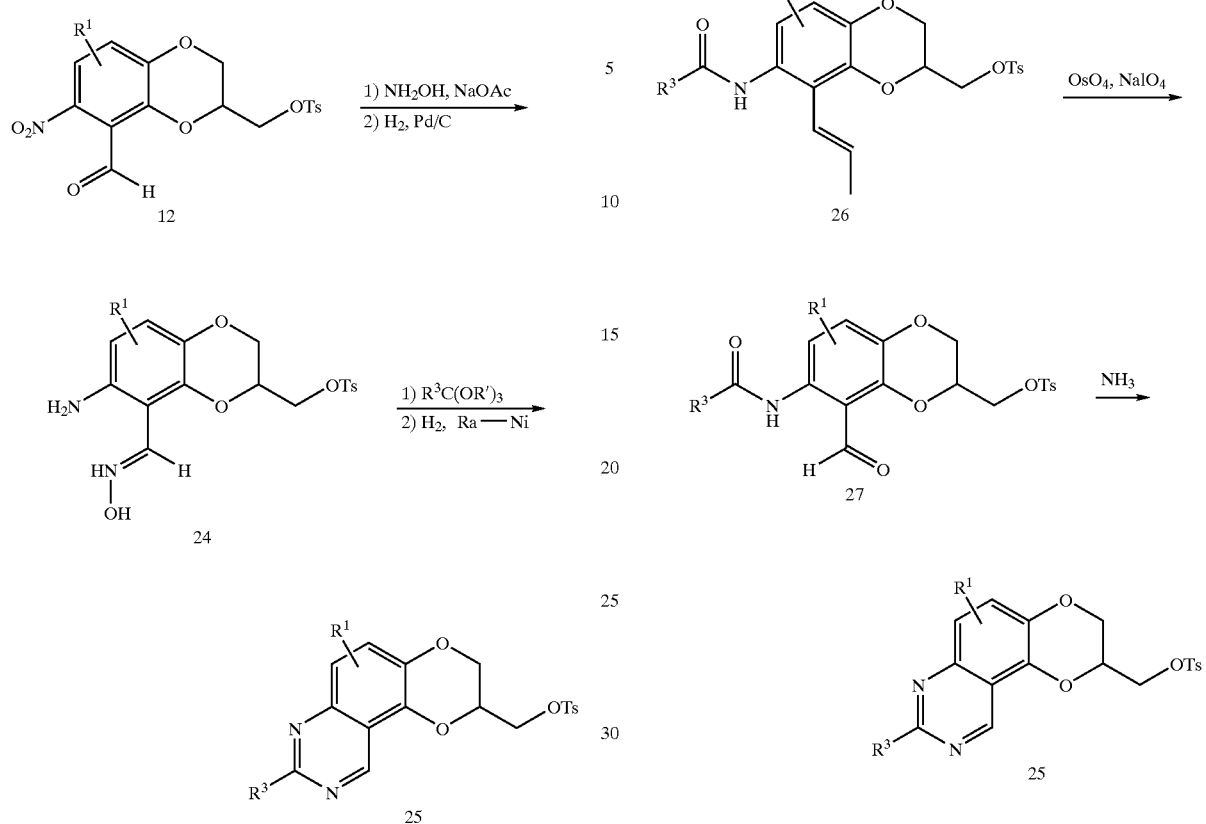

The 2,3-dihydro-1,4-dioxino[2,3-f]quinazolin-2-ylmethylamines of the invention may be alternatively prepared from the rearranged olefin described above by the method outlined in Scheme 9 below. The nitro olefin (10) is first reduced to the aniline by treatment with a suitable reducing agent such as stannous chloride dihydrate in refuxing ethyl acetate and the resulting amine acylated with the appropriate acyl halide or anhydride. The olefin (26) is then converted to the aldehyde (27) by cleavage with catalytic osmium tetroxide in the presence of excess sodium periodate. Cyclization directly to the 2,3-dihydro-1,4-dioxino[2,3-f]quinazoline-2-methyltosylate (25) or halide is effected by treatment of the amido aldehyde (27) with ammonia and replacement of the tosylate or halide with the appropriately substituted cycloalkylamine in some high boiling solvent such as dimethyl sulfoxide as described above gives the title compounds of the invention.

Scheme 9

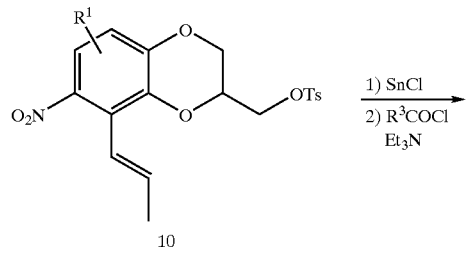

The 2,3-dihydro-1,4-dioxino[2,3-f]quinoxalin-2-ylmethylamines of the invention are prepared as illustrated in Scheme 10 below. The o-nitrobenzaldehyde (12) described above is oxidized to the o-nitrobenzoic acid (28) by a suitable oxidant such as chromium trioxide (Jones' oxidation) or sodium chlorite and the acid converted to the o-nitroaniline (29) with diphenylphosphoryl azide (DPPA) in the presence of a tertiary base such as diisopropylethylamine. Reduction of the resulting nitroaniline to the diamine (30) with hydrogen and palladium on carbon and cyclization by treatment with the appropriate dicarbonyl compound (for example, glyoxal, 2,3-butanedione, 3,4-hexanedione) gives the 2,3-dihydro-1,4-dioxino[2,3-f]quinoxaline-2-methyltosylate (31) or halide. Replacement of the tosylate or halide with the appropriately substituted cycloalkylamine in some high boiling solvent such as dimethyl sulfoxide gives the title compounds of the invention.

Scheme 10

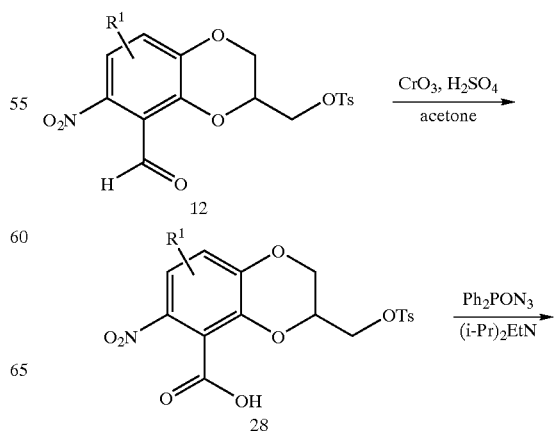

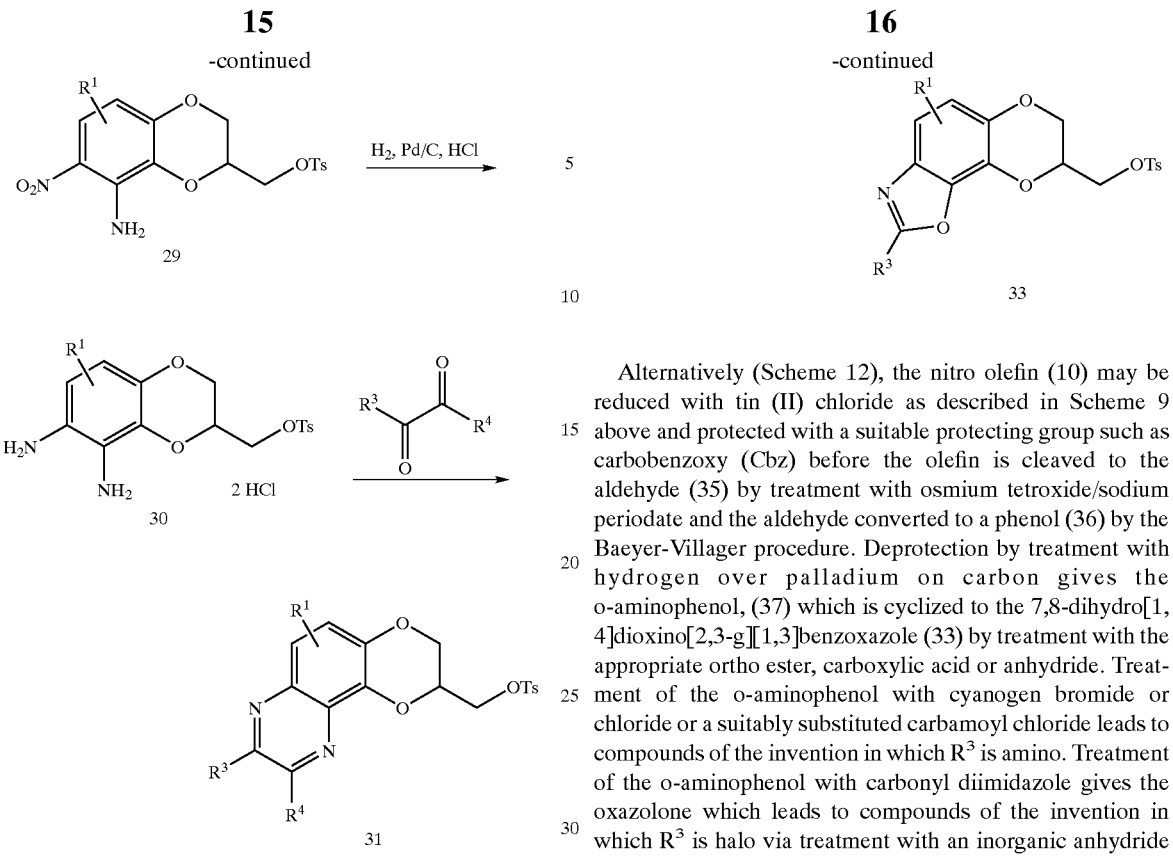

The 7,8-dihydro[1,4]dioxino[2,3-g][1,3]benzoxazol-8-ylmethylamines of the invention are prepared as illustrated in Scheme 11 below. The o-amidobenzaldehyde (27) described in Scheme 9 is converted to the phenol (32) by treatment with meta-chloroperoxybenzoic acid in a Baeyer-Villager reaction and cyclization to the 7,8-dihydro[1,4]dioxino[2,3-g][1,3]benzoxazole (33) is effected by treatment at reflux with an appropriate dehydrating agent such as an ortho ester or an acid catalyst such as p-toluenesulfonic acid. Replacement of the tosylate or halide with the appropriately substituted cycloalkylamine in some high boiling solvent such as dimethyl sulfoxide gives the title compounds of the invention.

Alternatively (Scheme 12), the nitro olefin (10) may be reduced with tin (II) chloride as described in Scheme 9 above and protected with a suitable protecting group such as carbobenzoxy (Cbz) before the olefin is cleaved to the aldehyde (35) by treatment with osmium tetroxide/sodium periodate and the aldehyde converted to a phenol (36) by the Baeyer-Villager procedure. Deprotection by treatment with hydrogen over palladium on carbon gives the o-aminophenol, (37) which is cyclized to the 7,8-dihydro[1,4]dioxino[2,3-g][1,3]benzoxazole (33) by treatment with the appropriate ortho ester, carboxylic acid or anhydride. Treatment of the o-aminophenol with cyanogen bromide or chloride or a suitably substituted carbamoyl chloride leads to compounds of the invention in which R³ is amino. Treatment of the o-aminophenol with carbonyl diimidazole gives the oxazolone which leads to compounds of the invention in which R³ is halo via treatment with an inorganic anhydride such as phosphoryl chloride or bromide. Replacement of the tosylate with the appropriately substituted cycloalkylamine as above gives the title compounds of the invention.

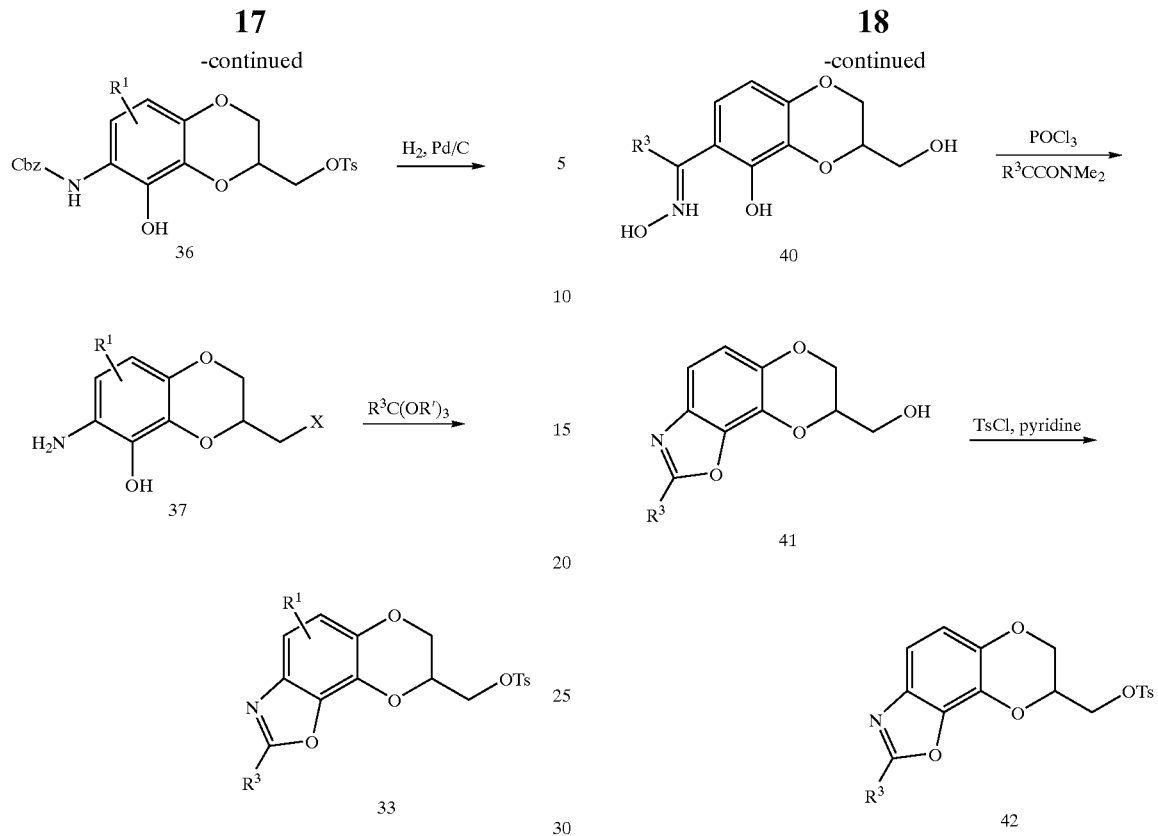

Compounds of the invention in which $R^1$ is hydrogen and $R^3$ is alkyl are most conveniently prepared according to Scheme 13 below. The appropriate 2',3',4'-trihydroxyacylphenone (38) is regioselectively alkylated with glycidyl tosylate or an epihalohydrin in the presence of a base such as sodium carbonate to give the corresponding 7-acyl-8-hydroxybenzodioxan-2-methanol (39). Following conversion of the ketone to the oxime (40) by reaction with hydroxylamine hydrochloride and sodium acetate, cyclization to the oxazole (41) is effected by treatment with phosphoryl chloride in the appropriate dimethylalkanoic acid amide. The resulting 7,8-dihydro-1,6,9-trioxa-3-aza-cyclopenta[a]naphthalene-8-methanol is converted to the tosylate (42) by treatment with p-toluenesulfonyl chloride in pyridine and combined with the appropriate cycloalkylamine as described above to give the title compounds of the invention.

The 7,8-dihydro-3H-6,9-dioxa-1,3-diaza-cyclopenta[a]naphthalenes of the invention are prepared as illustrated in Scheme 14 below. The diamine (30) described in Scheme 10 is cyclized by treatment at reflux with the appropriate carboxylic acid to give the imidazole (43). Refluxing the diamine dihydrochloride in higher boiling carboxylic acids occasionally causes replacement of a tosylate group with a chloride. Replacement of the tosylate or halide with the appropriately substituted piperidine in some high boiling solvent such as dimethyl sulfoxide gives the 7,8-dihydro-3H-6,9-dioxa-1,3-diaza-cyclopenta[a]naphthalenes of the invention in which $R^6$ is hydrogen, perfluoroalkyl or alkyl. Treatment of the diamine described above with cyanogen bromide or chloride or a suitably substituted carbamoyl chloride leads to compounds of the invention in which $R^6$ is amino. Treatment of the diamine with carbonyl diimidazole gives the imidazolone which leads to compounds of the invention in which $R^6$ is halo via treatment with an inorganic anhydride such as phosphoryl chloride or bromide. Replacement of the tosylate with the appropriately substituted cycloalkylamine as above gives the title compounds of the invention.

Scheme 13

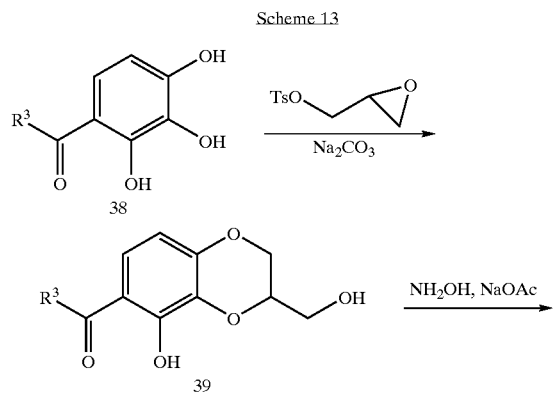

Scheme 14

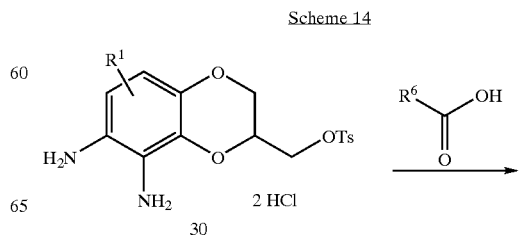

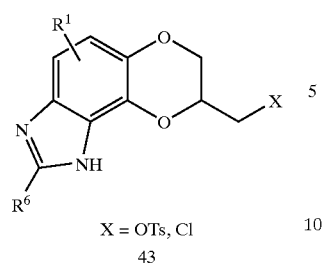

X = OTs, Cl
43

The 2,3-dihydro-7H-[1,4]dioxino[2,3-e]indoles of the invention are prepared as illustrated in Scheme 15 below. Specifically, the primary alcohol (9) from the Claisen rearrangement described in Scheme 4 is converted to the tosylate (44) by reaction with p-toluenesulfonyl chloride in the presence of a tertiary amine or pyridine, or alternatively to a halide by reaction with carbon tetrabromide or carbon tetrachloride in combination with triphenylphosphine. The allyl side chain is then cleaved to the aldehyde (45) by treatment with ozone at low temperature, followed by work-up with a tertiary base such as diisopropylethylamine or triethylamine, or by treatment with catalytic osmium tetroxide and sodium periodate. Reduction of the nitro group with hydrogen over platinum oxide leads directly to formation of the indole (46) in which $R^7$ is hydrogen. Alternatively, the aldehyde may be treated with an appropriate alkyl Grignard reagent or with trifluoromethyl trimethylsilane in the presence of cesium fluoride, then oxidized to a ketone with a suitable oxidant such as pyridinium chlorochromate (PCC) or the Swern reagent and reduced with hydrogen over platinum oxide to give the indoles in which $R^7$ is alkyl or trifluoromethyl. Replacement of the tosylate or halide with the appropriately substituted cycloalkylamine in some high boiling solvent such as dimethyl sulfoxide gives the title compounds of the invention.

Scheme 15

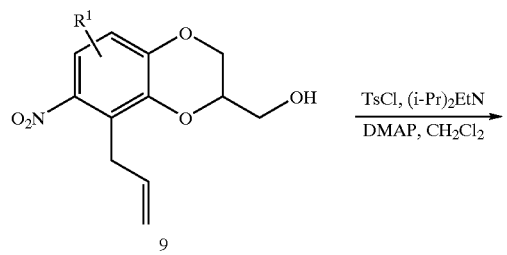

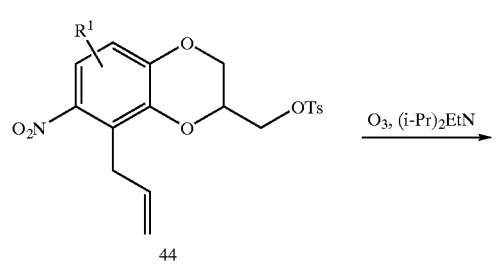

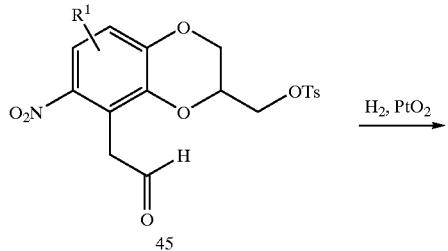

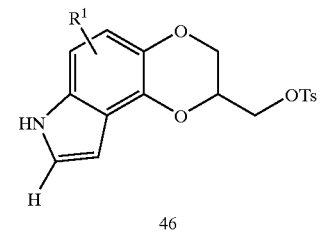

The 2,3-dihydro-7H-[1,4]dioxino[2,3-e]indoles of the invention may alternatively be prepared following procedure (Scheme 16). The o-nitrobenzaldehyde (12) is condensed with the appropriate nitroalkane in the presence of a suitable base catalyst to yield the corresponding o,β-dinitrostyrene (47). Reduction of both nitro groups with hydrogen over palladium on carbon is accompanied by cyclization to form the indole (48). Replacement of the tosylate with the appropriately substituted cycloalkylamine as above gives the title compounds of the invention.

Scheme 16

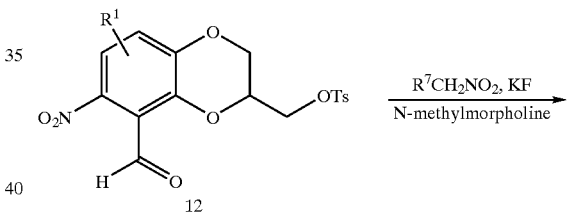

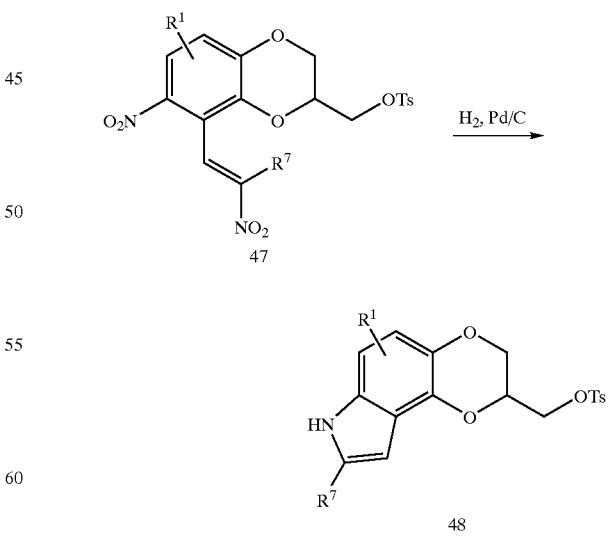

In yet another method, compounds of the present invention may be prepared in accordance with Scheme 17. The synthesis of compound I is comprised of steps that begin with halogenation of 49 where R' is alkyl of 1–6 carbon atoms, with reagents such as N-halosuccinimide in acetonitrile to give 50 (where Hal is halogen such as Br, Cl or I). Deprotection of 50 with Lewis acids such as boron tribromide, boron trichloride, aluminum trichloride, ferric chloride, or trimethylsilyl iodide in a suitable solvent such as methylene chloride, or with strong protic acids such as HBr and HCl gives the salt 51. Free base 51 may be obtained by neutralization with an Amberlyst A-21 resin slurry in polar solvents such as ethanol or methanol. Alkylation of 51, either as the free base or as the salt, with benzyl or substituted benzyl protected glycidyl ethers

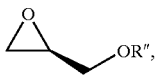

where R″ is benzyl, substituted benzyl such as 4-bromobenzyl, 3,4-dimethoxybenzyl, 2- or 4-nitrobenzyl, or 4-methoxybenzyl) in suitable polar solvents such as dimethyl sulfoxide, dimethyl formamide, or dimethyl acetamide in the presence of bases such as sodium carbonate, potassium carbonate, or triethylamine gives 52. The compound 52 is then cyclized using palladium catalysts such as tris(dibenzylideneacetone)dipalladium, tetrakis(triphenylphosphine)palladium, or palladium acetate with ligands from the group consisting of (±) BINAP and separate enantiomers thereof, (±) Tol-BINAP and separate enantiomers thereof; 1-1'-bis(diphenylphosphino) ferrocene, 1,3-bis(diphenylphosphino)propane, and 1,2 bis(diphenylphosphino)ethane in the presence of bases such as NaH, LiH, KH, potassium carbonate, sodium carbonate, titanium carbonate, cesium carbonate, potassium t-butoxide or potassium phosphate tribasic in a suitable solvent such as toluene, or alternatively, with copper catalyst such as copper iodide in the presence of bases such NaH, LiH, KH in a suitable solvent such as toluene to afford 53. Deprotection of 53 with Lewis acids such as boron tribromide, boron trichloride, aluminum trichloride, ferric chloride, trimethylsilyl iodide in a suitable solvent such as methylene chloride, or with strong protic acids such as HBr and HCl or under reductive cleavage conditions using Pd catalyst and hydrogen transfer reagents

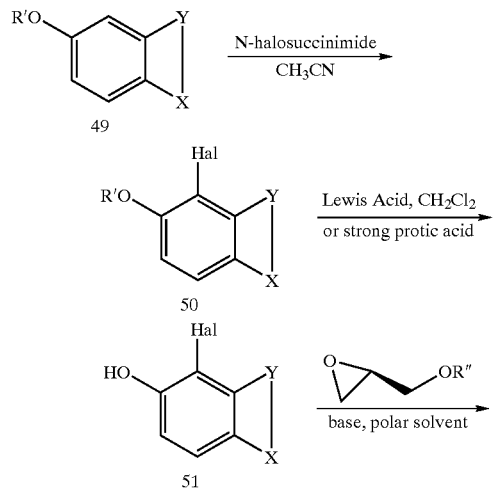

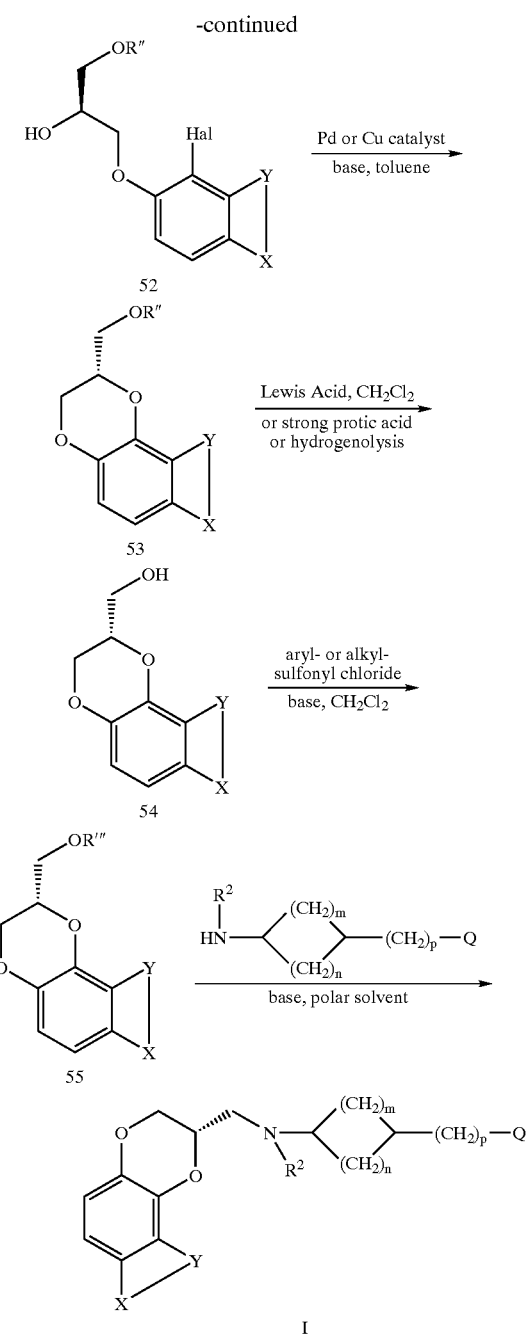

such as hydrogen, cyclohexene, methyl cyclohexene, or ammonium formate gives 54. The hydroxyl moiety of 54 can be activated with an aryl- or alkyl-sulfonyl chloride such as p-toluenesulfonyl chloride, methanesulfonyl chloride, 2-, 3- or 4-nitrobenzenesulfonyl chloride, or 2- or 4-bromobenzenesulfonyl chloride in the presence of bases such as triethylamine or pyridine in suitable solvents such as methylene chloride, THF, or toluene to afford 55 where R‴ is sulfonate such as p-toluenesulfonate, methanesulfonate, 2-, 3-, or 4-nitrobenzenesulfonate, or 2- or 4-bromobenzenesulfonate. The final coupling of 55 with cycloalkyamines appropriate to the invention, in the presence of bases such as diisopropyl ethylamine, potassium carbonate, or sodium carbonate in polar solvents such as THF, dioxane, DMSO, DMF, or DMA affords compounds of Formula I.

The substituted cycloalkylamines (2) relevant to the chemistry described Scheme 1 are prepared as shown in Scheme 18. Specifically, a suitably substituted cycloalkanone (56) is reacted with a secondary (R' is hydrogen) or tertiary amine (R' is alkyl) in the presence of a suitable reducing agent such as sodium triacetoxyborohydride or sodium cyanoborohydride to give the cyclopentyl amine 57. In this method the amine may be a benzodioxan methanamine (4) as described above (Scheme 2) to give the title compounds of the invention. Alternatively, the reductive amination of Scheme 18 may produce intermediate cycloalkylamines, which are then reacted with a suitably substituted benzodioxan methyltosylate (1) or bromide as in Scheme 1 to give the title compounds of the invention.

Scheme 18

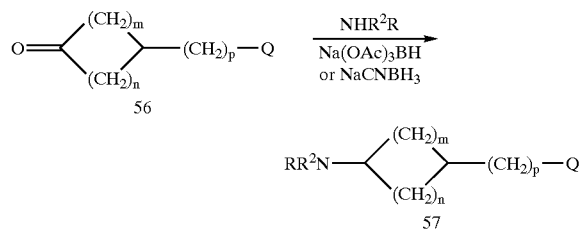

Intermediate cycloalkylamines in which R² is hydrogen are best prepared by using benzylamine (R' is benzyl) in the reductive amination of Scheme 18, followed by debenzylation of the amine 58 by transfer hydrogenation using ammonium formate and palladium on carbon in refluxing methanol (Scheme 19).

Scheme 19

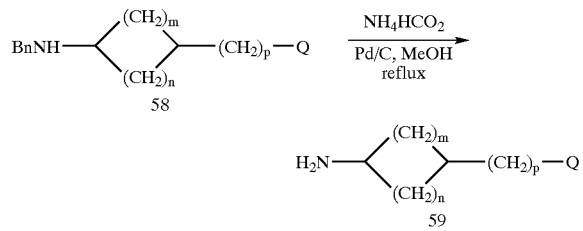

The cyclohexanones appropriate to the above chemistry are known compounds or can be prepared by one schooled in the art. The intermediate 3-indolylcyclopentanones (62) required for certain compounds of the invention may be prepared as shown in Scheme 20. Specifically, a suitably substituted indole (60) is reacted with cyclopentenone (61) in the presences of a Lewis acid to give the corresponding 3-indol-3-yl-cyclopenanone (62)

Scheme 20

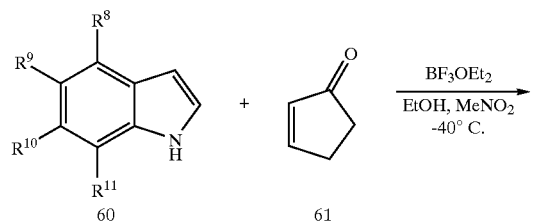

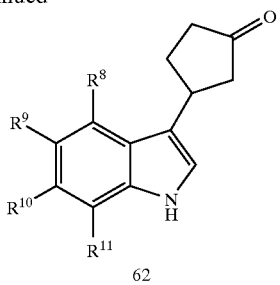

A protocol similar to that used by Cheetham et al. (*Neuropharmacol.* 32:737, 1993) was used to determine the affinity of the compounds of the invention for the serotonin transporter. The compound's ability to displace $^3$H-paroxetine from male rat frontal cortical membranes was determined using a Tom Tech filtration device to separate bound from free $^3$H-paroxetine and a Wallac 1205 Beta Plate® counter to quantify bound radioactivity. $K_i$'s thus determined for standard clinical antidepressants are 1.96 nM for fluoxetine, 14.2 nM for imipramine and 67.6 nM for zimelidine. A strong correlation has been found between $^3$H-paroxetine binding in rat frontal cortex and $^3$H-serotonin uptake inhibition.

High affinity for the serotonin $5HT_{1A}$ receptor was established by testing the claimed compound's ability to displace [$^3$H] 8-OH-DPAT (dipropylamino-tetralin) from the $5HT_{1A}$ serotonin receptor following a modification of the procedure of Hall, et al., *J. Neurochem.* 44, 1685 (1985), which utilizes CHO cells stably transfected with human $5HT_{1A}$ receptors. The $5HT_{1A}$ affinities for the compounds of the invention are reported below as $K_i$'s.

Antagonist activity at $5HT_{1A}$ receptors was established by using a $^{35}$S-GTPγS binding assay similar to that used by Lazareno and Birdsall (*Br. J. Pharmacol.* 109:1120, 1993), in which the test compound's ability to affect the binding of $^{35}$S-GTPγS to membranes containing cloned human $5HT_{1A}$ receptors was determined. Agonists produce an increase in binding whereas antagonists produce no increase but rather reverse the effects of the standard agonist 8-OH-DPAT. The test compound's maximum inhibitory effect is represented as the $I_{max}$, while its potency is defined by the $IC_{50}$.

The results of the three standard experimental test procedures described in the preceding three paragraphs were as follows:

| Compound | 5-HT Transporter Affinity $K_i$ (nM) | $5HT_{1A}$ Receptor Affinity $K_i$ (nM) | $5HT_{1A}$ Function $IC_{50}$ (nM) ($I_{max}$) |
|---|---|---|---|
| Example 1 | 1.25 | 2.56 | $EC_{50}$ = 33 ($E_{max}$ = 38%) |
| Example 2 | 1.69 | 12.81 | nd |
| Example 3 | 0.93 | 4.73 | 83 (100) |
| Example 3-Isomer A | 0.38 | 8.73 | 69 (82) |
| Example 3-Isomer B | 0.33 | 2.03 | 34 (97) |
| Example 4 | 0.62 | 9.12 | 44 (84) |
| Example 4-Isomer A | 0.54 | 7.72 | 60 (56) |
| Example 4-Isomer B | 0.67 | 26.5 | 1440 (100) |
| Example 5 | 3.69 | 5.35 | 142 (69) |
| Example 5-Isomer A | 2.11 | 12.5 | 190 (88) |
| Example 5-Isomer B | 3.00 | 1.91 | 158 (97) |
| Example 6 | 1.67 | 20.3 | 228 (55) |
| Example 7 | 19.0 | 51.7 | nd |

-continued

| Compound | 5-HT Transporter Affinity $K_i$ (nM) | $5HT_{1A}$ Receptor Affinity $K_i$ (nM) | $5HT_{1A}$ Function $IC_{50}$ (nM) ($I_{max}$) |
|---|---|---|---|
| Example 8 | 4.16 | 14.6 | $EC_{50}$ = 66 ($E_{max}$ = 95%) |
| Example 9 | 0.84 | 5.01 | 242 (100) |
| Example 10 | 1.38 | 28.55 | 172 (85) |
| Example 11 | 1.46 | 16.36 | 274 (100) |
| Example 12 | 11.0 | 84.37 | nd |
| Example 13 | 5.45 | 18.8 | 494 (100) |

Like the antidepressants fluoxetine, paroxetine and sertraline, the compounds of this invention have the ability to potently block the reuptake of the brain neurotransmitter serotonin. They are thus useful for the treatment of diseases commonly treated by the administration of serotonin selective reuptake inhibitor (SSRI) antidepressants, such as depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder (including trichotillomania), social anxiety disorder, generalized anxiety disorder, obesity, eating disorders such as anorexia nervosa and bulimia nervosa, vasomotor flushing, cocaine and alcohol addiction, sexual dysfunction (including premature ejaculation), and related illnesses. Moreover, many of the compounds of this invention have potent affinity for and antagonist activity at brain $5HT_{1A}$ serotonin receptors. Recent clinical trials employing drug mixtures (e.g., fluoxetine and pindolol) have demonstrated a more rapid onset of antidepressant efficacy for a treatment combining SSRIs activity and $5HT_{1A}$ antagonism (Blier and Bergeron, 1995; F. Artigas et al., 1996; M. B. Tome, et al., 1997). The compounds of the invention are thus exceedingly interesting and useful for treating depressive illnesses. Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in Remington's Pharmaceutical Sciences, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions that are sterile solutions or suspensions can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide, as used herein, means either directly administering a compound or composition of the present invention, or administering a prodrug, derivative or analog which will form an equivalent amount of the active compound or substance within the body.

The present invention includes prodrugs of compounds of Formula I, Ia and Ib. Prodrug, as used herein, means a compound which is convertible in vivo by metabolic means (e.g. by hydrolysis) to a compound of Formula I. Various forms of prodrugs are known in the art, for example, as discussed in Bundgaard, (ed.), *Design of Prodrugs*, Elsevier (1985); Widder, (ed.), *Methods in Enzymology*, vol. 4, Academic Press (1985); Krogsgaard-Larsen, et al., (ed). *Design and Application of Prodrugs, Textbook of Drug Design and Development*, Chapter 5, 113–191 (1991), Bundgaard, et al., *Journal of Drug Deliver Reviews*, 8:1–38 (1992), Bundgaard, *J. of Pharmaceutical Sciences*, 77:285 et seq. (1988); and Higuchi and Stella (eds.) *Prodrugs as Novel Drug Delivery Systems*, American Chemical Society (1975).

The following examples illustrate the production of representative compounds of this invention.

INTERMEDIATE 1

3-Allyloxy-4-methoxynitrobenzene 97.5 g (0.51 mole) of the sodium salt of 5-nitroguaiacol was dissolved in one liter of DMF and 1.5 equivalents of allyl bromide added. The reaction was heated to 65° C. for two hours, after which time much of the dark color had discharged and tlc (1:1 $CH_2Cl_2$/hexane) indicated loss of starting material. The solvent was concentrated in vacuum and the residue washed with water. The product was isolated by filtration and dried in a vacuum. This gave 112 g of pale yellow solid. A sample recrystallized from methanol, gave m.p. 93–94° C.

INTERMEDIATE 2

2-Allyloxy-4-nitrophenol

To one liter of dimethyl sulfoxide was added 750 mL of 2 N aqueous sodium hydroxide and the mixture was heated to 65° C. The pale yellow solid 3-allyloxy-4-methoxynitrobenzene prepared above was added in portions over a 30 minute period and then the temperature was raised to 95° C. and maintained for 3 hours, after which time the starting material had been consumed. The mixture was allowed to cool and poured into a mixture of 1 L ice and 1 L 2 N HCl. 73 Grams of crude but homogeneous (by tlc 1:1 $CH_2Cl_2$/hexane) desired product was isolated as a light brown solid by filtration. This material was subsequently dissolved in 1:1 hexane/methylene chloride and filtered through silica gel to give 68 g of pale yellow solid, which, when recrystallized from ethyl/acetate/hexane, gave m.p. 61–62° C. The aqueous mother liquors from the initial crystallization above were extracted with 2 L of ethyl acetate. This was dried over sodium sulfate, filtered and evaporated to a dark oil. Column chromatography on silica with 1:1 $CH_2Cl_2$/hexane gave an additional 12 g of the title compound as a yellow solid. Elution with 2% MeOH in $CHCl_3$ gave 12 g of a dark oil which slowly crystallized in vacuum. This proved to be the Claisen product, 3-allyl-4-nitrocatechol.

intermediate 3

2-(2-Allyloxy-4-nitrophenoxymethyl)-oxirane 20 g (0.50 mole) of 60% NaH/mineral oil was placed in a two liter flask and washed with 500 mL of hexane. 1 L of DMF was added, followed by 77 g (0.40 mole) of the 2-allyloxy-4-nitrophenol prepared in the previous step. Addition of the phenol was performed in portions under argon. After stirring the mixture for 30 minutes at room temperature under argon, 108 g (0.48 moles) of (R)-glycidyl tosylate was added and the mixture heated at 70–75° C. under nitrogen overnight. Upon cooling, the DMF was removed in vacuum and replaced with one liter of methylene chloride. This was washed with 500 mL portions of 2 N HCl, saturated sodium bicarbonate and saturated brine and dried over sodium sulfate. The mixture was filtered, concentrated to an oil in vacuum and column chromatographed on silica gel using 1:1 hexane/methylene chloride as eluent. This gave 43 g of product contaminated with traces of the two starting materials, followed by 21 g of pure product as a pale yellow solid. The impure material was recrystallized from 1.2 L of 10% ethyl acetate/hexane to give 34 g of pure (homogeneous on silica gel tlc with 1:1 hexane/methylene chloride) (R)-2-(2-allyloxy-4-nitrophenoxymethyl)-oxirane: m.p. 64° C.

Elemental Analysis for: $C_{12}H_{13}NO_5$
Calc'd: C, 57.37; H, 5.21; N, 5.58
Found: C, 57.50; H, 5.21; N, 5.43

INTERMEDIATE 4

(8-Allyl-7-nitro-2,3-dihydro-benzo(1,4)dioxin-2-yl)-methanol (R)-2-(2-Allyloxy-4-nitrophenoxymethyl)-oxirane (20 g, 80 mmoles) prepared as above was heated at 155° C. in mesitylene for 24 hours under nitrogen. Filtration of the black solid which formed gave 1.5 g of very polar material. Evaporation of the solvent in vacuum followed by column chromatography on silica gel with methylene chloride as eluent gave 10 g of recovered starting material and 7.5 g of the desired rearranged (S)-(8-allyl-7-nitro-2,3-dihydro-benzo(1,4)dioxin-2-yl)-methanol, which slowly crystallized on standing in vacuum (m.p. 67° C.). The yield based on recovered starting material is 75%.

Elemental Analysis for: $C_{12}H_{13}NO_5$
Calc'd: C, 57.37; H, 5.21; N, 5.58
Found: C, 57.26; H, 5.20; N, 5.35

INTERMEDIATE 5

Toluene-4-sulfonic acid 8-allyl-7-nitro-2,3-dihydro-benzo(1,4)dioxin-2-ylmethyl ester 9.55 g (38.0 mmole) of (S)-(8-allyl-7-nitro-2,3-dihydro-benzo(1,4)dioxin-2-yl)-methanol was dissolved in 465 mL of pyridine, 29.0 g (152 mmole) of p-toluenesulfonyl chloride was added and the mixture stirred at room temperature under nitrogen overnight. Water was then added to quench the excess tosyl chloride and the solvent was removed in vacuum and replaced with methylene chloride. This solution was washed with 2 N HCl, with saturated sodium bicarbonate, and with saturated brine, and dried over magnesium sulfate. Filtration, evaporation in vacuum and column chromatography on silica gel with 1:1 hexane/methylene chloride as eluent gave 12.6 g (92%) of toluene-4-sulfonic acid (R)-allyl-7-nitro-2,3-benzo(1,4)dioxin-2-ylmethyl ester, which slowly crystallized to a tan solid (m.p. 60–62° C.) upon standing.

Elemental Analysis for: $C_{19}H_{19}NO_7S$
Calc'd: C, 56.29; H, 4.72; N, 3.45
Found: C, 56.13; H, 4.58; N, 3.44

INTERMEDIATE 6

{7-Nitro-8-[1-propenyl]-2,3-dihydro-1,4-benzodioxin-2-yl}methyl 4-methylbenzenesulfonate To a solution of 10.0 g (24.0 mmole) of (R)-[8-allyl-7-nitro-2,3-dihydro-1,4-benzodioxin-2-yl]methyl 4-methylbenzenesulfonate in 700 mL of benzene was added 1.03 g of bis(acetonitrile)dichloropalladium (II) and the mixture was refluxed under nitrogen for 48 hours. The catalyst was then removed by filtration and the filtrate concentrated in vacuum to a brown oil. Column chromatography on silica gel with methylene chloride as eluent gave 7.2 g of the title compound as a mixture of E and Z isomers. A sample of {(2R)-7-nitro-8[(E)-1-propenyl]-2,3-dihydro-1,4-benzodioxin-2-yl}methyl 4-methylbenzenesulfonate was obtained as a yellow solid (m.p. 105–106° C.) by evaporation of a pure E isomer-containing fraction.

Elemental Analysis for: $C_{19}H_{19}NO_7S$
Calc'd: C, 56.29; H, 4.72; N, 3.45
Found: C, 56.12; H, 4.64; N, 3.39

INTERMEDIATE 7

(8-Formyl-7-nitro-2,3-dihydro-1,4-benzodioxin-2-yl)methyl 4-methylbenzenesulfonate {(2R)-7-Nitro-8-[1-propenyl]-2,3-dihydro-1,4-benzodioxin-2-yl}methyl 4-methyl-benzenesulfonate (10.5 g, 25.9 mmole) dissolved in 400 mL of methylene chloride was treated with excess ozone at −78° C. Diisopropylethylamine (11.5 mL, 66.0 mmole) was then added dropwise over 30 minutes and the mixture allowed to come to room temperature and stir overnight under a nitrogen atmosphere. The mixture was then diluted to 600 mL with methylene chloride, washed three times with 100 mL portions of 2N HCl (aq), twice with 200 mL portions of saturated aqueous sodium bicarbonate and with 200 mL of saturated brine. The solution was dried over magnesium sulfate, filtered and concentrated in vacuum to a crude brown oil, which was column chromatographed on silica gel with 10% hexane/methylene chloride to give 7.52 g of the (R)-enantiomer of the title compound as a yellow solid. $^1$H-NMR (CDCl$_3$): doublet 7.8 δ (2 H); doublet 7.62 δ (1 H); doublet 7.4 δ (2 H); doublet 7.0 δ (1 H); multiplet 4.4–4.6 δ (2 H); multiplet 4.2 δ (3 H); singlet 2.4 δ (3 H).

INTERMEDIATE 8

{7-Nitro-8-[(E)-3-oxo-1-butenyl]-2,3-dihydro-1,4-benzodioxin-2-yl}methyl 4-methylbenzenesulfonate To a solution of 3.00 g (7.37 mmole) of [(2R)-8-formyl-7-nitro-2,3-dihydro-1,4-benzodioxin-2-yl]methyl 4-methylbenzenesulfonate in 250 mL of toluene was added 2.90 g (9.10 mmole) of 1-triphenylphosphoranylidene-2-propanone. The mixture was stirred at room temperature under nitrogen for 5 hours, during which time some product precipitated from solution. The solvent was removed in vacuum and the crude residue was column chromatographed on silica gel with methylene chloride as eluent to give 3.0 g of the (R)-enantiomer of the title compound as a yellow solid. $^1$H-NMR (CDCl$_3$): doublet 7.8 δ (2 H); doublet 7.6 δ (1 H); doublet 7.5 δ (2 H); doublet 7.4 δ (2 H); doublet 6.95 δ (1 H); doublet 6.6 δ (1 H); multiplet 4.5 δ (1 H); doublet of doublets 4.0 δ (1 H); multiplet 4.2 δ (3 H); singlet 2.45 δ (3 H); singlet 2.4 δ (3 H).

INTERMEDIATE 9

(8-Methyl-2,3-dihydro[1,4]dioxino[2,3-f]quinolin-2-yl)methyl 4-methylbenzenesulfonate To a solution of {(2R)-7-nitro-8-[(E)-3-oxo-1-butenyl]-2,3-dihydro-1,4-benzo-dioxin-2-yl}methyl 4-methylbenzenesulfonate (3.40 g, 7.83 mmole) in 200 mL of acetic acid/ethanol (3:2) was added 2.25 g (40.2 mmole) of iron powder and the mixture was heated at reflux under nitrogen for 8 hours. After the reaction was complete, 150 mL of water was added and the mixture filtered through a pad of celite. The filtrate was neutralized with saturated aqueous sodium bicarbonate and extracted with ethyl acetate. The extract was dried over magnesium sulfate, filtered and evaporated in vacuum. The residue was column chromatographed on silica gel using a gradient elution commencing with 20% ethyl acetate/hexane and ending with 70% ethyl acetate/hexane to give 2.5 g of the (R)-enantiomer of the title compound as a yellow oil. $^1$H-NMR (CDCl$_3$): doublet 8.1 δ (1 H); doublet 7.6 δ (2H); doublet 7.45 δ (1H); multiplet 7.2 δ (4H); multiplet 4.6 δ (1 H); multiplet 4.3 δ (3 H); multiplet 4.1 δ (1H); singlet 2.5 δ (3 H); singlet 2.4 δ (3 H).

INTERMEDIATE 10

1-[5-Hydroxy-3-(hydroxymethyl)-2,3-dihydro-1,4-benzodioxin-6-yl]-1-ethanone

To a solution of 2',3',4'-trihydroxyacetophenone (10.6 g, 63.0 mmole) in DMF (75 mL) was added potassium carbonate (17.4 g, 126 mmole). After 5 minutes (R)-glycidyl tosylate (9.67 g, 42.3 mmole) was added, then the heterogeneous mixture was heated to 70° C. for 3 hours. After removal of the solvent in vacuum, the residue was taken into water (800 mL) and was then extracted with ethyl acetate (4×300 mL). The combined organic layers were dried over magnesium sulfate, filtered and evaporate to dryness in vacuum. The crude brown oil thus obtained was column chromatographed on silica gel with 40% hexane/ethyl acetate as eluent to give the (S)-enantiomer of the title compound as a yellow oil which solidifies upon standing (7.5 g, 78%). MS (ESI) m/z 223 (M−H)−.

Elemental Analysis for: $C_{11}H_{12}O_5 \cdot 0.10H_2O$
Calc'd: C, 58.46; H, 5.44
Found: C, 58.02; H, 5.09

INTERMEDIATE 11

1-[5-Hydroxy-3-(hydroxymethyl)-2,3-dihydro-1,4-benzodioxin-6-yl]-1-ethanone oxime A solution of hydroxylamine hydrochloride (2.38 g, 34.2 mmole) in 1:1 ethanol/pyridine (100 mL) was added to a solution of 1-[(3S)-5-hydroxy-3-(hydroxymethyl)-2,3-dihydro-1,4-benzodioxin-6-yl]-1-ethanone (1.92 g, 8.57 mmole) in ethanol (200 mL). It was then heated to reflux under nitrogen for 5 hours. Upon cooling, the solvent was removed and replaced with ethyl acetate. The solution was then washed with water (200 mL) and with aqueous 2N HCl (100 mL), dried over magnesium sulfate, filtered and evaporated in vacuum to give 1.89 g (93%) of the (S)-enantiomer of the title compound as a gray solid, m.p. 162° C. MS (ESI) m/z 240 (M+H)+.

Elemental Analysis for: $C_{11}H_{13}NO_5 \cdot 0.35H_2O$
Calc'd: C, 53.81; H, 5.62; N, 5.71
Found: C, 53.51; H, 5.30; N, 5.58

INTERMEDIATE 12

[2-Methyl-7,8-dihydro[1,4]dioxino[2,3-g][1,3]benzoxazol-8-yl]methanol 3.03 g (12.6 mmole) of 1-[(3S)-5-hydroxy-3-(hydroxymethyl)-2,3-dihydro-1,4-benzodioxin-6-yl]-1-ethanone oxime was dissolved in a mixture of 1:3 N,N-dimethylacetamide/acetonitrile (100 mL). The solution was cooled in an ice/water bath and a solution of phosphorus oxychloride (1.26 mL, 35 mmole) in 1:3 N,N-dimethylacetamide/acetonitrile (30 mL) was added. The reaction mixture was stirred under nitrogen over a period of 48 hours. It was then added to an ice cold, saturated solution of sodium acetate, extracted with ethyl acetate, dried over magnesium sulfate, filtered and evaporated in vacuum. The resulting crude oil was column chromatographed on silica gel with 60% hexane/ethyl acetate to remove impurities and the product eluted with 40% hexane/ethyl acetate. After evaporation of the solvent in vacuum, 2.08 g (75%) of the (S)-enantiomer of the title compound was obtained as a white solid, m.p. 120° C. MS (ESI) m/z 222 (M+H)+.
Elemental Analysis for: $C_{11}H_{11}NO_4 \cdot 0.20H_2O$
Calc'd: C, 58.77; H, 5.11; N, 6.23
Found: C, 58.93; H, 4.91; N, 6.14

INTERMEDIATE 13

[2-Methyl-7,8-dihydro[1,4]dioxino[2,3-g][1,3]benzoxazol-8-yl]methyl 4-methylbenzenesulfonate To a solution of [(8S)-2-methyl-7,8-dihydro[1,4]dioxino[2,3-g][1,3]benzoxazol-8-yl]methanol (1.80 g, 8.14 mmole) in methylene chloride (100 mL) was added p-toluenesulfonyl chloride (3.90 g, 20.4 mmole). The mixture was cooled in an ice bath and a solution of diisopropylethylamine (3.55 mL, 20.4 mmole) in methylene chloride (20 mL) was then added dropwise, followed by 4-dimethylaminopyridine (0.65 g, 5.30 mmole). The solution was allowed to warm to room temperature and was stirred under nitrogen overnight. The reaction was diluted to 500 mL in volume with methylene chloride, then washed with aqueous 2 N HCl (200 mL), with saturated aqueous sodium bicarbonate (200 mL), and with brine (150 mL), dried over magnesium sulfate, filtered and evaporated in vacuum to a yellow oil. The crude oil was column chromatographed on silica gel using methylene chloride to remove impurities and 3% methanol/methylene chloride to elute the (R)-enantiomer of the title compound, which becomes a white solid under vacuum (2.56 g, 84%), m.p. 123° C. MS (ESI) m/z 376 (M+H)+.
Elemental Analysis for: $C_{18}H_{17}NO_6S \cdot 0.20H_2O$
Calc'd: C, 57.04; H, 4.63; N, 3.70
Found: C, 56.75; H, 4.62; N, 3.51

INTERMEDIATE 14

3-(5-Fluoro-1H-indol-3-yl)-cyclopentanone

A mixture of 5-fluoroindole (6.0 g, 44.4 mmol) and 2-cyclopenten-1-one (4.5 mL, 53.3 mmol) in nitromethane (22 mL) was cooled to −20° C. in a carbon tetrachloride-dry ice bath. A mixture of boron trifluoride etherate (1.6 mL, 11.1 mmol) and ethanol (2.2 mL, 43 mmol) was added dropwise from an addition funnel. The reaction mixture was stirred at −20° C. for 2 hours, then was quenched with 5% aqueous sodium bicarbonate solution (100 mL), and extracted with ethyl acetate (3×200 mL). The combined organic layers were washed with water (100 mL) and brine (100 mL), then were dried over anhydrous sodium sulfate, filtered and concentrated to give 9.5 g of the title compound. Trituration with ethyl acetate afforded 5.6 g (58%) of the title compound as a yellow solid. An analytical sample was recrystallized from ethyl acetate/methanol: mp 119–120° C.; MS (ESI) m/z 218 [M+H]+.
Elemental Analysis for: $C_{13}H_{12}FNO$
Calc'd: C, 71.81; H, 5.57; N, 6.45
Found: C, 71.52; H, 5.41; N, 6.35

INTERMEDIATE 15

3-(1H-indol-3-yl)-cyclopentanone

This compound was prepared in similar manner as for Intermediate 14, using indole (2.34 g, 20 mmol) and 2-cyclopenten-1-one (2.0 mL, 24.0 mmol) to give 1.7 g (44%) of the desired product as a thick oil: MS (ESI) m/z 200 [M+H]+.
Elemental Analysis for: $C_{13}H_{13}NO$
Calc'd: C, 78.36; H, 6.58; N, 7.03
Found: C, 78.21; H, 6.49; N, 7.10

INTERMEDIATE 16

3-(5-Fluoro-1-methyl-1H-indol-3-yl)-cyclopentanone

A suspension of sodium hydride (60% dispersion in oil, 0.335 g, 8.2 mmol) in dimethylformamide (20 mL) was stirred at room temperature. A solution of 3-(5-fluoro-1H-indol-3-yl)-cyclopentanone (1.5 g, 6.9 mmol) in 10 mL of DMF was added dropwise over 10 min. The reaction mixture was stirred at room temperature for an additional 30 min, then iodomethane (3.1 g, 21.8 mmol) was added. After stirring at room temperature for 24 hours, the reaction mixture was poured into water (100 mL) and extracted with ethyl acetate (2×100 mL). The combined organic layers were washed with water (50 mL) and brine (50 mL), then were dried over anhydrous sodium sulfate, filtered, and concentrated to give 1.6 g of crude product. Flash chromatography on silica gel (50% ethyl acetate/hexane) afforded 1.2 g (81%) of the title compound as a thick oil which solidified on standing. An analytical sample was recrystallized from ethyl acetate/hexane: mp 104–105° C.; MS (ESI) m/z 232 [M+H]+.
Elemental Analysis for: $C_{14}H_{14}FNO$
Calc'd: C, 72.71; H, 6.10; N, 6.06
Found: C, 72.48; H, 5.97; N, 5.96

INTERMEDIATE 17

N-Benzyl-3-(5-fluoro-1H-indol-3-yl)-cyclopentylamine

A mixture 3-(5-fluoro-1H-indol-3-yl)-cyclopentanone (1.0 g, 4.61 mmol), benzylamine (0.54 g, 5.05 mmol) and glacial acetic acid (0.7 mL, 1.08 mmol) were stirred at room temperature for 30 minutes. Sodium triacetoxy borohydride (1.5 g; 7.11 mmole) was added portionwise over a 10 minutes period. The reaction was stirred at room temperature for 24 hours. The reaction mixture was poured into 1 N aqueous NaOH (80 mL) and extracted with ethyl acetate (3×100 mL). The combined organic layers were washed with $H_2O$ (100 mL) and brine (100 mL), then were dried over anhydrous sodium sulfate, filtered and concentrated to give 1.5 g of a thick yellow oil. Flash chromatography on silica gel (7% 2 M $NH_3$ in methanol/ethyl acetate) afforded 0.5 g of the cis isomer (first eluting) and 0.5 g of the trans isomer.

Cis isomer: MS (ESI) m/z 309 [M+H]$^+$.
Elemental Analysis for: $C_{20}H_{21}$, $FN_2 \cdot 0.50H_2O$
Calc'd: C, 75.68; H, 6.99; N, 8.83
Found: C, 75.91; H, 6.67; N, 8.70
Trans isomer: MS (ESI) m/z 309 [M+H]$^+$.
Elemental Analysis for: $C_{20}H_{21}FN_2$
Calc'd: C, 77.89; H, 6.86; N, 9.08
Found: C, 77.22; H, 6.91; N, 9.31

INTERMEDIATE 18

N-Benzyl-3-(1H-indole-3-yl)-cyclopentylamine

This compound was prepared in similar manner as for Intermediate 17, using 3-(1H-indol-3-yl)-cyclopentanone (3.0 g, 15 mmol) and benzylamine (1.95 g, 18 mmol) to give 4.7 g of the desired product as a mixture of cis and trans isomers, which were separated by flash chromatography to afford 0.6 g of the cis isomer (first eluting) and 1.0 g of the trans isomer.
Cis Isomer: MS (ESI) m/z 291 [M+H]$^+$.
Elemental analysis for: $C_{20}H_{22}N_2 \cdot 0.25H_2O$(Cis A)
Calc'd: C, 72.49; H, 7.15; N, 8.45
Found: C, 72.75; H, 7.12; N, 8.46
Trans Isomer: MS (ESI) m/z 291 [M+H]$^+$.
Elemental analysis for: $C_{20}H_{22}N_2 \cdot 0.25H_2O$(trans-B)
Calc'd: C, 72.49; H, 7.15; N, 8.45
Found: C, 72.46; H, 7.04; N, 8.47

INTERMEDIATE 19

N-Benzyl-3-(5-fluoro-1-methyl-1H-indol-3yl)-cyclopentylamine

This compound was prepared in the same manner as for Intermediate 17, using 3-(5-fluoro-1-methyl-1H-indol-3-yl)-cyclopentanone (1.25 g, 5.19 mmol) and benzylamine (0.66 g, 6.2 mmol) to afford 1.7 g of the desired product as a mixture of cis and trans isomers. Flash chromatography on silica gel (3% 2 M $NH_3$ in methanol/ethyl acetate) afforded 0.4 g (23%) of the cis isomer and 0.45 g (27%) of the trans isomer.
Cis Isomer: MS (ESI) m/z 323 [M+H]$^+$.
Elemental Analysis for: $C_{21}H_{23}FN_2 \cdot 0.25H_2O$
Calc'd: C, 77.15; H, 7.25; N, 8.57
Found: C, 77.38; H, 7.19; N, 8.53
Trans isomer: MS (ESI) m/z 323 [M+H]$^+$.
Elemental Analysis for: $C_{21}H_{23}FN_2 \cdot 0.10H_2O$
Calc'd: C, 77.79; H, 7.21; N, 8.64
Found: C, 77.68; H, 6.99; N, 8.69

INTERMEDIATE 20 cis-Benzyl-[4-(5-fluoro-1-H-indol-3-yl-)-cyclohexyl]-amine

This compound was prepared in similar manner as for Intermediate 17, using 4-(5-Fluoro-1-H-indol-3-yl)-cyclohexanone (0.6 g, 2.6 mmol) and benzylamine (0.3 g, 2.8 mmol) to afford 1.0 of the desired product as a mixture of cis and trans isomers. Flash chromatography on silica gel (3% 2M $NH_3$ in methanol/ethyl acetate) afforded 0.41 g (65%) of cis isomer and 0.22 g (33%) of the trans isomer.
Cis isomer: MS (ESI) m/z 323 [M+H]$^+$.
Elemental Analysis for: $C_{21}H_{23}FN_2 \cdot 0.1H_2O$
Calc'd: C, 77.79; H, 7.21; N, 8.64
Found: C, 77.44; H, 7.48; N, 8.87
Trans isomer: MS (ESI) m/z 323 [M+H]$^+$.
Elemental Analysis for: $C_{21}H_{23}FN_2$
Calc'd: C, 78.23; H, 7.19; N, 8.69
Found: C, 78.08; H, 7.49; N, 8.97

INTERMEDIATE 21 cis-3-(5-Fluoro-1H-indol-3-yl)-cyclopentylamine

A mixture of cis-benzyl-3-(5-fluoro-1H-indol-3-yl)-cyclopentylamine (0.45 g, 1.46 mmol), 0.2 g 10% Pd/C and ammonium formate (1.0 g, 15.9 mmol) in methanol (30 mL) were refluxed under nitrogen for 4 hours. The reaction mixture was cooled, filtered through celite, and concentrated. The residue was diluted with 1 N aqueous NaOH (50 mL) and extracted with ethyl acetate (3×50 mL). The combined organic layers were washed with water (50 mL) and brine (50 mL), then were dried over anhydrous sodium sulfate, filtered and concentrated to give 0.28 g (100%) of the title compound as a thick oil: MS (ESI) m/z 219 [M+H]$^+$.
Elemental Analysis for: $C_{13}H_{15}FN_2 \cdot 0.20H_2O$
Calc'd: C, 70.37; H, 7.00; N, 12.63
Found: C, 70.65; H, 6.86; N, 12.67

INTERMEDIATE 22 trans-3-(5-Fluoro-1H-indol-3-yl)-cyclopentylamine

A mixture of trans-benzyl-3-(5-fluoro-1H-indol-3-yl)-cyclopentylamine (0.45 g, 1.46 mmol), 0.20 g 10% Pd/C, and ammonium formate (1.0 g, 15.9 mmol) in methanol (30 mL) were refluxed under nitrogen for 4 hours. The reaction mixture was cooled, filtered through celite, and concentrated. The residue was diluted with 1 N aqueous NaOH (50 mL) and extracted with ethyl acetate (3×50 mL). The combined organic layers were washed with water (50 mL) and brine (50 mL), then were dried over anhydrous sodium sulfate, filtered, and concentrated to give 0.28 g (100%) of the title compound as a thick oil: MS (ESI) m/z 219 [M+H]$^+$.
Elemental Analysis for: $C_{13}H_{15}FN_2 \cdot 0.10H_2O$
Calc'd: C, 71.54; H, 6.93; N, 12.83
Found: C, 71.09; H, 6.67; N, 12.59

INTERMEDIATE 23 cis-3-(1H-Indol-3-yl)-cyclopentylamine

This compound was prepared in the same manner as for Intermediate 20, using cis-benzyl-3-(1H-indol-3-yl)-cyclopentylamine (1.3 g, 4.48 mmol) and ammonium formate (1.6 g, 25.3 mmol) to afford 0.8 g (90%) of the desired product as a thick oil which solidified upon standing: MS (ESI) m/z 201 [M+H]$^+$.
Elemental analysis for: $C_{13}H_{16}N_2 \cdot 0.1H_2O$
Calc'd: C, 77.27; H, 8.08; N, 13.86
Found: C, 77.26; H, 8.17; N, 13.73

INTERMEDIATE 24 trans-3-(1H-Indol-3-yl)-cyclopentylamine

This compound was prepared in the same manner as for Intermediate 20, using trans-benzyl-3-(1H-indol-3-yl)-cyclopentylamine (0.8 g, 2.8 mmol) and ammonium formate (1.1 g, 17.5 mmol) to afford 0.49 g (89%) of the desired product as a thick oil, which solidified upon standing: MS (ESI) m/z 201 [M+H]$^+$.
Elemental analysis for: $C_{13}H_{16}N_2$
Calc'd: C, 77.96; H, 8.05; N, 13.99
Found: C, 77.63; H, 8.06; N, 13.71

INTERMEDIATE 25 cis-3-(5-Fluoro-1-methyl-1H-indol-3-yl)-cyclopentylamine

This compound was prepared in the same manner as for Intermediate 20, using cis-benzyl-3-(5-fluoro-1-methyl-1H-indol-3-yl)-cyclopentylamine (0.4 g, 1.2 mmol) to give 0.2 g (71%) of the title compound as a thick oil, which was used in the next reaction without purification: MS (ESI) m/z 233 $[M+H]^+$.

INTERMEDIATE 26 trans-3-(5-Fluoro-1-methyl-1H-indol-3-yl)-cyclopentylamine

This compound was prepared in the same manner as for Intermediate 20, using trans-benzyl-3-(5-fluoro-1-methyl-1H-indol-3-yl)-cyclopentylamine (0.42 g, 1.3 mmol) to give 0.3 g (79%) of the title compound as a thick oil, which was used in the next reaction without purification: MS (ESI) m/z 233 $[M+H]^+$.
Elemental Analysis for: $C_{14}H_{17}FN_2.0.25H_2O$
Calc'd: C, 71.01; H, 7.45; N, 11.83
Found: C, 71.14; H, 7.52; N, 11.67

INTERMEDIATE 27 cis-4-(5-Fluoro-1H-indol-3-yl)-cyclohexylamine

This compound was prepared in the same manner as for Intermediate 20, using cis-benzyl-4-(5-fluoro-1-H-indol-3-yl)-cyclohexylamine (0.41 g, 1.3 mmol) to give 0.24 g (81%) of the desired amine as a white solid: mp 186–188° C.; MS (ESI) m/z 233 $[M+H]^+$.
Elemental Analysis for: $C_{14}H_{17}FN_2.0.1H_2O$
Calc'd: C, 71.83; H, 7.41; N, 11.97
Found: C, 71.78; H, 7.62; N, 11.80

INTERMEDIATE 28 trans-4-(5-Fluoro-1H-indol-3-yl)-cyclohexylamine

This compound was prepared in the same manner as for Intermediate 20, using trans-benzyl-4-(5-fluoro-1-H-indol-3-yl)-cyclohexylamine (0.21 g, 0.65 mmol) to give 0.135 g (89%) of the desired amine as a white solid: mp 205–208° C.; MS (ESI) m/z 233 $[M+H]^+$.
Elemental Analysis for: $C_{14}H_{17}FN_2.0.25H_2O$
Calc'd: C, 71.01; H, 7.45; N, 11.83
Found: C, 70.99; H, 7.58; N, 11.80

EXAMPLE 1

N-[(cis)-3-(1H-indol-3-yl)cyclopentyl]-N-{[(2S)-8-methyl-2,3-dihydro[1,4]dioxino[2,3-f]quinolin-2-yl]methyl}amine A mixture of toluene-4-sulfonic acid 8-methyl-2,3-dihydro-[1,4]dioxino[2,3-f]quinolin-2-yl methyl ester (0.3 g, 0.77 mmol) and cis-3-(1H-indol-3-yl)-cyclopentylamine (0.26 g, 1.30 mmol) in DMSO (10 mL) were heated at 80° C. for 30 hours. The cooled reaction mixture was poured into 1 N aqueous NaOH (50 mL) and extracted with ethyl acetate (3×50 mL). The combined organic layers were washed with water (50 mL) and brine (50 mL), then were dried over anhydrous sodium sulfate, filtered, and concentrated to give 0.5 g of crude product. Flash chromatography on silica gel afforded 0.06 g (18%) of the desired product as its fumarate salt: MS (ESI) m/z 414 $[M+H]^+$.
Elemental Analysis for: $C_{26}H_{27}N_3O_2.C_4H_4O_4$
Calc'd: C, 68.04; H, 5.90; N, 7.93
Found: C, 67.80; H, 6.07; N, 7.93

EXAMPLE 2

N-[(trans)-3-(1H-indol-3-yl)cyclopentyl]-N-{[(2S)-8-methyl-2,3-dihydro[1,4]dioxino[2,3-f]quinoli-2-yl]methyl}amine This compound was prepared in a manner similar to Example 1, using toluene-4-sulfonic acid 8-methyl-2,3-dihydro-[1,4]dioxino[2,3-f]quinolin-2-yl methyl ester (0.3 g, 0.77 mmol) and trans-3-(1H-indol-3-yl)-cyclopentylamine (0.26 g, 1.30 mmol) to give 0.06 g (18%) of the desired product as its fumarate salt: MS (ESI) m/z 414 $[M+H]^+$.
Elemental Analysis for: $C_{26}H_{27}N_3O_2.C_4H_4O_4$
Calc'd: C, 68.04; H, 5.90; N, 7.93
Found: C, 67.76; H, 5.99; N, 8.23

EXAMPLE 3

N-[(cis)-3-(5-fluoro-1H-indol-3-yl)cyclopentyl]-N-{[(2S)-8-methyl-2,3-dihydro[1,4]dioxino[2,3-f]quinolin-2-yl]methyl}amine Toluene-4-sulfonic acid 8-methyl-2,3-dihydro-[1,4]dioxino[2,3-f]quinolin-2-yl methyl ester (0.48 g, 1.2 mmole) and cis-3-(5-fluoro-1H-indol-3-yl)-cyclopentylamine (0.35 g, 1.6 mmole) were combined in 5 mL of DMSO under nitrogen. This solution was stirred and heated at 100° C. under nitrogen for 5 hours. After the reaction was allowed to stand at room temperature overnight it was stirred and heated at 100° C. for 3 hours more. The solvent was evaporated at reduced pressure. The residue was partitioned between EtOAc and water. The organic layer was washed with water twice, dried over magnesium sulfate and concentrated in vacuum. The crude residue was column chromatographed on silica gel with a gradient of EtOAC and hexane. Ther residue was dissolved in EtOH and an excess of HCl/EtOH was added. Filtration of the precipitate afforded 0.14 g of the title compound as a light yellow solid: mp>230° C. (dec), MS (APCI) m/z 432 $(M+H)^+$.
Elemental Analysis for: $C_{26}H_{26}FN_3O_2.2HCl.0.5H_2O$
Calc'd: C, 60.82; H, 5.69; N, 8.18
Found: C, 60.50; H, 5.76; N, 7.75

The diastereomers of a 220 mg sample of the above compound were separated by preparative chiral HPLC (Chiralcel OD 25×2 cm, 20% of 0.1% diethylamine/ethanol in hexane)

Isomer A: N-[(1R*,3S*)-3-(5-fluoro-1H-indol-3-yl)cyclopentyl]-N-{[(2S)-8-methyl-2,3-dihydro[1,4]dioxino[2,3-f]quinolin-2-yl]methyl}amine: 0.08 g as a colorless oil. This was dissolved in EtOH and added to fumaric acid (0.0236 g, 0.203 mmole). Filtration gave 0.0846 g of the title compound as a white powder: m.p. 232–233° C., MS (ESI) m/z 432 $(M+H)^+$.
Elemental Analysis for: $C_{26}H_{26}FN_3O_2.C_4H_4O_4.0.25H_2O$
Calc'd: C, 65.27; H, 5.57; N, 7.61
Found: C, 65.20; H, 5.50; N, 7.56

Isomer B: N-[(1S*,3R*)-3-(5-fluoro-1H-indol-3-yl)cyclopentyl]-N-{[(2S)-8-methyl-2,3-dihydror[1,4]dioxino[2,3-f]quinolin-2-yl]methyl}amine: 0.0781 g as a colorless oil. This was dissolved in EtOH and added to fumaric acid (0.0223 g, 0.192 mmole). Filtration gave 0.0763 g of the title compound as a white powder: m.p. 234–235° C., MS (ESI) m/z 432 $(M+H)^+$.
Elemental Analysis for: $C_{26}H_{26}FN_3O_2.C_4H_4O_4$ Calc'd: C, 65.80; H, 5.52; N, 7.67
Found: C, 65.50; H, 5.39; N, 7.57

EXAMPLE 4

N-[(trans)-3-(5-fluoro-1H-indol-3-yl)cyclopentyl]-
N-{[(2S)-8-methyl-2,3-dihydro[1,4]dioxino[2,3-f]
quinoli-2-yl]methyl}amine Toluene-4-sulfonic acid (2R)-8-methyl-2,3-dihydro-[1,4]
dioxino[2,3-f]quinolin-2-ylmethyl ester (0.40 g, 1.0 mmole)
and trans-3-(5-fluoro-1H-indol-3-yl)-cyclopentylamine
(0.30 g, 1.4 mmole) were combined in 3 mL of DMSO. This
solution was stirred at 100° C. under nitrogen for 18 hours.
The reaction was cooled to room temperature. The DMSO
was evaporated under reduced pressure. The residue was
partitioned between ethyl acetate and saturated aqueous
sodium carbonate. The organic phase was washed twice with
water, once with brine, dried over magnesium sulfate and
concentrated in vacuum to give an oil. The crude residue was
column chromatographed on silica gel using a gradient of
EtOAC and hexane to give 0.15 g of the title compound as
a yellow oil. To a solution of this in EtOH was added fumaric
acid (0.0399 g, 0.344 mmole) in EtOH. Filtration gave
0.1471 g of the title compound as a light yellow powder:
dec.>245° C., MS (ESI) m/z 432 (M+H)$^+$.
Elemental Analysis for: $C_{26}H_{26}FN_3O_2.0.5C_4H_4O_4.0.75H_2O$
Calc'd: C, 66.85; H, 5.91; N, 8.35
Found: C, 66.91; H, 5.58; N, 8.02

The diastereomers of an 88 mg sample of the above
compound were separated by preparative chiral HPLC
(Chiralcel OD 25×2 cm, ethanol).
Isomer A: N-[(1S*,3S*)-3-(5-fluoro-1H-indol-3-yl)
cyclopentyl]-N-{[(2S)-8-methyl-2,3-dihydro[1,4]dioxino
[2,3-f]quinolin-2-yl]methyl}amine: 0.0211 g as an oil.
This was dissolved in EtOH and fumaric acid (0.0061 g,
0.053 mmole) was added. Filtration gave 0.0173 g of the
title compound (hemi-fumarate) as a white solid fumarate:
mp>250° C. (dec).
Isomer B: N-[(1R*,3R*)-3-(5-fluoro-1H-indol-3-yl)
cyclopentyl]-N-{[(2S)-8-methyl-2,3-dihydro[1,4]dioxino
[2,3-f]quinolin-2-yl]methyl}amine: 0.025 as oil. This was
dissolved in EtOH and fumaric acid (0.0071 g, 0.061
mmole) was added. Filtration gave 0.0180 g of the title
compound (hemi-fumarate) as a white powder: m.p.
207–210° C.

EXAMPLE 5

N-[(cis)-3-(5-fluoro-1-methyl-1H-indol-3-yl)
cyclopentyl]-N-{[(2S)-8-methyl-2,3-dihydro[1,4]
dioxino[2,3-f]quinoli-2-yl]methyl}amine This compound was prepared in a manner similar to
Example 1, using toluene-4-sulfonic acid 8-methyl-2,3-
dihydro-[1,4)dioxino[2,3-f]quinolin-2-yl methyl ester (0.42
g, 1.09 mmol) and 3-cis-(5-fluoro-1-methyl-1H-indol-3-yl)-
cyclopentylamine (0.32 g, 1.4 mmol) to afford 0.16 g (33%)
of the desired product as a thick oil which was converted to
the fumarate salt: MS (ESI) m/z 446 [M+H]$^+$.
Elemental Analysis for: $C_{27}H_{28}FN_3O_2.C_4H_4O_4$ e $H_2O$
Calc'd: C, 64.24; H, 5.91; N, 7.25
Found: C, 64.10; H, 5.73; N, 6.98

The diastereomers of a 340 mg sample of the above
compound were separated by preparative chiral HPLC
(Chiralcel OD 25×2 cm, 0.1% diethylamine/ethanol).
Isomer A: R$_T$=9.78 min: N-[(1R*,3S*)-3-(5-fluoro-1-
methyl-1H-indol-3-yl)cyclopentyl]-N-{](2S)-8-methyl-2,
3-dihydro[1,41]dioxino[2,3-f]quinoli-2-yl]methyl}amine
was characterized as its hemi-fumarate salt, hemi-hydrate
(white solid): mp 199–200° C.; MS (ESI) m/z 446
[M+H]$^+$; [α]$_D$–24.0° (c 1.0, DMSO
Elemental Analysis for:
$C_{27}H_{28}FN_3O_2.0.50C_4H_4O_4.0.50H_2O$
Calc'd: C, 67.95; H, 6.10; N, 8.20
Found: C, 67.61; H, 5.77; N, 7.91
Isomer B: R$_T$=11.24 min: N-[(1S*,3R*)-3-(5-fluoro-1-
methyl-1H-indol-3-yl)cyclopentyl]-N-{[(2S)-8-methyl-2,
3-dihydro[1,4]dioxino[2,3-f]quinoli-2-yl]methyl}amine
was characterized as its fumarate salt (white solid): mp
200–201° C.; MS (ESI) m/z 446 [M+H]$^+$; [a]$_D$–32.4° (c
0.54, DMSO)
Elemental Analysis for: $C_{27}H_{28}FN_3O_2$
Calc'd: C, 66.30; H, 5.74; N, 7.33
Found: C, 66.10; H, 5.70; N, 7.33

EXAMPLE 6

N-[(trans)-3-(5-fluoro-1-methyl-1H-indol-3-yl)
cyclopentyl]-N-{[(2S)-8-methyl-2,3-dihvro[1,4]
dioxino[2,3-f]quinolin-2-yl]methyl}amine This compound was prepared in a manner similar to
Example 1, using toluene-4-sulfonic acid 8-methyl-2,3-
dihydro-[1,4]dioxino[2,3-f]quinolin-2-yl methyl ester (0.49
g, 1.27 mmol) and trans-3-(5-fluoro-1-methyl-1H-indol-3-
yl)-cyclopentylamine (0.41 g, 1.8 mmol) to afford 0.26 g
(56%) of the desired product as a thick oil which was
converted to the fumarate salt: MS (ESI) m/z 446 [M+H]$^+$.
Elemental Analysis for: $C_{27}H_{28}FN_3O_2.C_4H_4O_4$
Calc'd: C, 66.30; H, 5.74; N, 7.48
Found: C, 65.93; H, 5.82; N, 7.35

EXAMPLE 7

(cis)-N-[4-(5-fluoro-1H-indol-3-yl)cyclohexyl]-N-{
[(2S)-8-methyl-2,3-dihydro[1,4]dioxino[2,3-f]
quinolin-2-yl]methyl}amine This compound was prepared in a manner similar to
Example 1, using toluene-4-sulfonic acid 8-methyl-2,3-
dihydro-[1,4]dioxino[2,3-f]quinolin-2-ylmethyl ester (0.5 g,
1.29 mmol) and cis-4-(5-fluoro-1H-indol-3-yl)-
cyclohexylamine (0.4 g, 1.72 mmol) to give 0.116 g (20%)
product as an oxalate salt: MS (ESI) m/z 446 [M+H]$^+$.
Elemental Analysis for: $C_{27}H_{28}FN_3O_2.C_2H_2O_4.1.5H_2O$
Calc'd: C, 61.91; H, 5.91; N, 7.47
Found: C, 62.03; H, 5.34; N, 7.10

EXAMPLE 8

(trans)-N-[4-(5-fluoro-1H-indol-3-yl)cyclohexyl]-N-
{[(2S)-8-methyl-2,3-dihydro[1,4]dioxino[2,3-f]
quinolin-2-yl]methyl}amine This compound was prepared in a manner similar to
Example 1, using toluene-4-sulfonic acid 8-methyl-2,3-
dihydro-[1,4]dioxino[2,3-f]quinolin-2-ylmethyl ester (0.5 g,
1.29 mmol) and trans-4-(5-fluoro-1H-indol-3-yl)-
cyclohexylamine (0.4 g, 1.72 mmol) to give 0.09 g (18%)
product as the fumarate salt: MS (ESI) m/z 446 [M+H]$^+$.
Elemental Analysis for: $C_{27}H_{28}FN_3O_2.C_4H_4O_4$
Calc'd: C, 66.30; H, 5.74; N, 7.48
Found: C, 66.54; H, 5.94; N, 7.91

EXAMPLE 9

N-[(cis)-3-(5-fluoro-1H-indol-3-yl)cyclopentyl]-N-
methyl-N-{[(2S)-8-methyl-2,3-dihydro[1,4]dioxino
[2,3-f]quinolin-2-yl]methyl}amine To a suspension of N-[(cis)-3-(5-fluoro-1H-indol-3-yl)
cyclopentyl]-N-{[(2S)-8-methyl-2,3-dihydro[1,4]dioxino[2, 3-f]quinolin-2-yl]methyl} fumarate (Example 3-Isomer B, 190 mg, 0.347 mmol) and 100 μL (1.41 mmol) of formaldehyde solution in 2 mL of THF was added sodium triacetoxyborohydride (300 mg, 1.41 mmol). The resulting mixture was stirred at ambient temperature for 24 hours. At that time, additional formaldehyde (100 μL, 1.41 mmol) and sodium triacetoxyborohydride (275 mg, 1.30 mmol) were added. After stirring an additional 3 hours, the reaction was diluted with saturated aqueous sodium bicarbonate solution (40 mL) and extracted with dichloromethane (3×25 mL). The combined organic layers were washed with brine (40 mL), then were dried over anhydrous sodium sulfate, filtered, and concentrated in vacuo. Flash chromatography (2×20 cm $SiO_2$, 3% $MeOH/CH_2Cl_2$) afforded 126 mg (82%) of the desired product, which was converted to its fumarate salt as a yellow solid: $[\alpha]_D$-1.9° (c 1.0, MeOH); MS (ESI) m/z 445 [M]$^+$.
Elemental Analysis for:
$C_{27}H_{28}FN_3O_2 \cdot C_4H_4O_4 \cdot 1.5H_2O \cdot 0.10C_4H_8O_2$
Calc'd: C, 63.13; H, 6.04; N, 7.03
Found: C, 63.41; H, 5.69; N, 6.64

EXAMPLE 10

N-[(trans)-3-(5-Fluoro-1H-indol-3-yl)cyclopentyl]-N-{[(8S)-2-methyl-7,8-dihydro[1,4]dioxino[2,3-g][1,3]benzoxazol-8-yl]methyl}amine Toluene-4-sulfonic acid (8R)-2-methyl-7,8-dihydro-1,6,9-trioxa-3-aza-cyclo-penta[a]naphthlen-8-ylmethyl ester (0.46 g, 1.2 mmole) and 3-(5-fluoro-1H-indol-3-yl)-cyclopentylamine (0.27 g, 1.2 mmole) were combined in 8 mL of DMSO under nitrogen. This solution was heated to 75-80° C. under nitrogen for 5 hours. After cooling to room temperature, the reaction was partitioned between ethyl acetate and saturated aqueous sodium bicarbonate. The organic phase was washed with brine, dried over magnesium sulfate and concentrated in vacuo. Flash chromatography on silica gel ($CH_2Cl_2$ then 1% $MeOH/CH_2Cl_2$) afforded 0.175 g of the title compound as an off-white solid: m.p. 79–82° C.; MS (ESI) m/z 422 (M+H)$^+$.
Elemental Analysis for: $C_{24}H_{24}FN_3O_3 \cdot 0.18CH_2Cl_2$
Calc'd: C, 66.50; H, 5.62; N, 9.62
Found: C, 66.87; H, 5.79; N, 9.25

EXAMPLE 11

N-[(cis)-3-(5-Fluoro-1H-indol-3-yl)cyclopentyl]-N-{[(8S)-2-methyl-7,8-dihydro[1,4]dioxino[2,3-g][1,3]benzoxazol-8-yl]methyl}amine Toluene-4-sulfonic acid (8R)-2-methyl-7,8-dihydro-1,6,9-trioxa-3-aza-cyclopenta-[a]naphthylen-8-ylmethyl ester (0.38 g, 1.0 mmole) and 3-(5-Fluoro-1H-indol-3-yl)-cyclopentylamine (0.50 g, 2.3 mmole) were combined in 8 mL of DMSO under nitrogen. This solution was heated to 80° C. under nitrogen for 5 hours. After cooling to room temperature, the reaction was partitioned between ethyl acetate and saturated aqueous sodium bicarbonate. The organic phase was washed with brine, dried over magnesium sulfate and concentrated in vacuo. Flash chromatography on silica gel ($CH_2Cl_2$ then 1% $MeOH/CH_2Cl_2$) afforded 0.23 g of the title compound as a white solid: m.p. 79–82° C.; MS (ESI) m/z 422 (M+H)$^+$.
Elemental Analysis for: $C_{24}H_{24}FN_3O_3$
Calc'd: C, 68.39; H, 5.74; N, 9.97
Found: C, 68.52; H, 6.11; N, 9.58

EXAMPLE 12

N-[(cis)-4-(5-fluoro-1H-indol-3-yl)cyclohexyl-N-{[(8S)-2-methyl-7,8-dihydro[1,4]dioxino[2,3-g][1,3]benzoxazol-8-yl]methyl}amine Toluene-4-sulfonic acid (8R)-2-methyl-7,8-dihydro-1,6,9-trioxa-3-aza-cyclopenta[a]naphthlen-8-ylmethyl ester (0.52 g, 1.39 mmole) and cis-4-(5-fluoro-1H-indol-3-yl)-cyclohexylamine (0.60 g, 2.6 mmole) were combined in 10 mL of anhydrous DMSO under nitrogen. This solution was heated to 80° C. under nitrogen for 5 hours. After cooling to room temperature, the reaction was partitioned between ethyl acetate and saturated aqueous sodium bicarbonate. The organic phase was washed with brine, dried over magnesium sulfate and concentrated in vacuo. Flash chromatography on silica gel ($CH_2Cl_2$ then 1% $MeOH/CH_2Cl_2$) afforded 0.26 g of the title compound as a light yellow solid: m.p. 80–82° C.; MS (ESI) m/z 436 (M+H)$^+$.

Elemental Analysis for: $C_{25}H_{26}FN_3O_3 \cdot 0.16C_6H_{14} \cdot 0.04 CH_2Cl_2$
Calc'd: C, 68.99; H, 6.31; N, 9.28
Found: C, 68.92; H, 6.71; N, 8.89

EXAMPLE 13

N-[(1R*,3S*)-3-(5-fluoro-1H-indol-3-yl)cyclopentyl]-N-methyl-N-{[(2S)-8-methyl-2,3-dihydro[1,4]dioxino[2,3-f]quinolin-2-yl]methyl}amine To a mixture of N-[(1R*,3S*)-3-(5-fluoro-1H-indol-3-yl)cyclopentyl]-N-{[(2S)-8-methyl-2,3-dihydro[1,4]dioxino[2,3-f]quinolin-2-yl]methyl}amine fumarate (200 mg, 0.365 mmol) and formaldehyde (37%, 50 μL, 0.67 mmol) in 2:1 tetrahydrofuran/methanol (3 mL) was added sodium triacetoxyborohydride (155 mg, 0.73 mmol). The reaction was allowed to stir at ambient temperature overnight, then was quenched with saturated aqueous sodium bicarbonate (20 mL) and extracted with ethyl acetate (3×20 mL). The combined organic layers were washed with brine (30 mL), dried over anhydrous sodium sulfate, filtered, and concentrated in vacuo. Flash chromatography (2×20 cm silica gel, 3% methanol/methylene chloride) afforded 115 mg (70%) of the title compound as a semi-solid, which was converted to its fumarate salt as a white powder: mp 198–199° C. (dec); MS (ES) m/z 446 [M+H]$^+$. $[\alpha]_D$ 5.3° (c 1.0, DMSO)

Elemental Analysis for: $C_{27}H_{28}FN_3O_2 \cdot 0.5C_4H_4O_4 \cdot 0.5H_2O$
Calc'd: C, 67.95; H, 6.10; N, 8.20
Found: C, 68.16; H, 5.88; N, 7.98

When ranges are used herein for physical properties, such as molecular weight, or chemical properties, such as chemical formulae, all combinations and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula I:

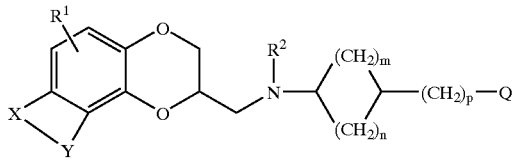

wherein:

$R^1$ is hydrogen, hydroxy, halo, cyano, carboxamido, carboalkoxy of 2 to 6 carbon atoms, trifluoromethyl, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen or alkyl of 1 to 6 carbons;

the group X—Y is —N=C($R^3$)—C($R^4$)=N—, —N=C($R^3$)—C($R^5$)=CH—, —N=C($R^3$)—N=CH—, —N=C($R^3$)—O—, —NH—C($R^6$)=N— or —NH—C($R^7$)=CH—;

$R^3$ and $R^4$ are, independently, hydrogen, halo, amino, mono- or di-alkylamino in which each alkyl group has 1 to 6 carbon atoms or alkyl of 1 to 6 carbon atoms;

$R^5$ is hydrogen or alkyl of 1 to 6 carbon atoms;

$R^6$ is hydrogen, halo, trifluoromethyl, pentafluoroethyl, amino, mono- or di-alkylamino in which each alkyl group has 1 to 6 carbon atoms or alkyl of 1 to 6 carbon atoms;

$R^7$ is hydrogen, halo, trifluoromethyl, pentafluoroethyl or alkyl of 1 to 6 carbon atoms;

Q is a heteroaryl moiety selected from the following:

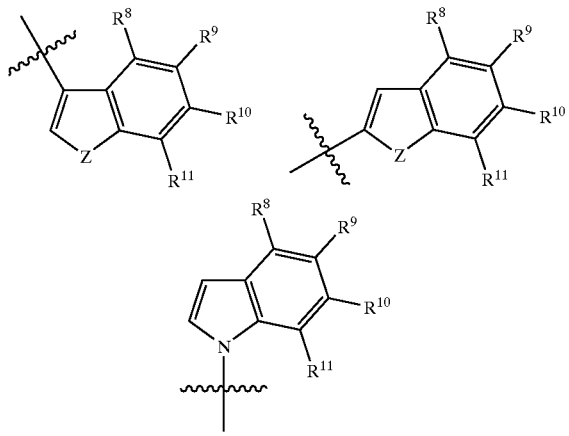

wherein Z is $NR^{12}$, S, or O;

$R^8$, $R^9$, $R^{10}$, and $R^{11}$ are, independently, hydrogen, hydroxy, halo, cyano, carboxamido, carboalkoxy of 2 to 6 carbon atoms, trifluoromethyl, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^{12}$ is hydrogen or alkyl of 1 to 6 carbon atoms;

m is 1 to 3;

n is 1 to 2; and p is 0 to 3;

or pharmaceutically acceptable salts thereof.

2. A compound according to claim 1, wherein n is 2 and m is 1 or pharmaceutically acceptable salts thereof.

3. A compound according to claim 1, wherein p is 0 or pharmaceutically acceptable salts thereof.

4. A compound according to claim 1, wherein the group X—Y is —N=C($R^3$)—C($R^5$)=CH— or —N=C($R^3$)—O— or pharmaceutically acceptable salts thereof.

5. A compound according to claim 1, wherein Q is a heteroaryl moiety of the formula

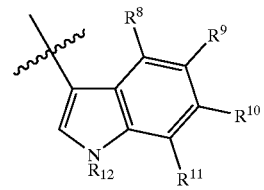

or pharmaceutically acceptable salts thereof.

6. A compound according to claim 1 having Formula Ia:

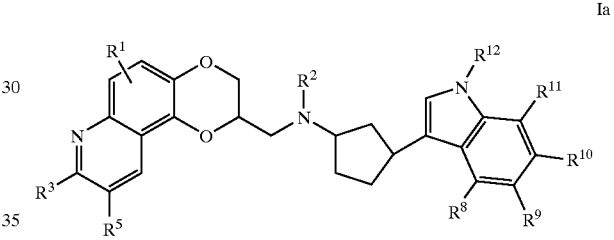

or a pharmaceutically acceptable salt thereof.

7. A compound according to claim 1 having Formula Ib:

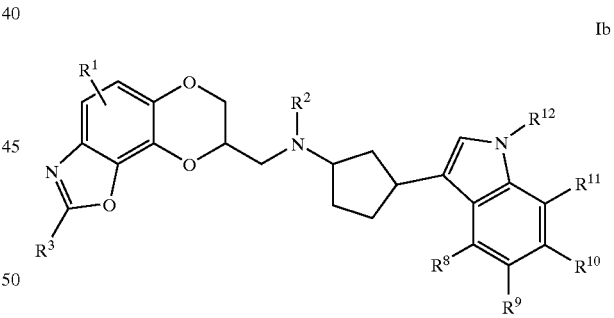

or a pharmaceutically acceptable salt thereof.

8. A compound according to claim 1, wherein said compound is N-[(cis)-3-(1H-indol-3-yl)cyclopentyl]-N-{[(2S)-8-methyl-2,3-dihydro[1,4]dioxino[2,3-f]quinolin-2-yl]methyl}amine or a pharmaceutically acceptable salt thereof.

9. A compound according to claim 1, wherein said compound is N-[(trans)-3-(1H-indol-3-yl)cyclopentyl]-N-{[(2S)-8-methyl-2,3-dihydro(1,4]dioxino[2,3-f]quinolin-2-yl]methyl}amine or a pharmaceutically acceptable salt thereof.

10. A compound according to claim 1, wherein said compound is N-[(cis)-3-(5-fluoro-1H-indol-3-yl)cyclopentyl]-N-{[(2S)-8-methyl-2,3-dihydro[1,4]dioxino[2,3-f]quinolin-2-yl]methyl}amine or a pharmaceutically acceptable salt thereof.

11. A compound according to claim 1, wherein said compound is N-[(1R,3S)-3-(5-fluoro-1H-indol-3-yl)cyclopentyl]-N-{[(2S)-8-methyl-2,3-dihydro[1,4]dioxino[2,3-f]quinolin-2-yl]methyl}amine or a pharmaceutically acceptable salt thereof.

12. A compound according to claim 1, wherein said compound is N-[(1S,3R)-3-(5-fluoro-1H-indol-3-yl)cyclopentyl]-N-{[(2S)-8-methyl-2,3-dihydro[1,4]dioxino[2,3-f]quinolin-2-yl]methyl}amine or a pharmaceutically acceptable salt thereof.

13. A compound according to claim 1, wherein said compound is N-[(trans)-3-(5-fluoro-1H-indol-3-yl)cyclopentyl]-N-{[(2S)-8-methyl-2,3-dihydro[1,4]dioxino[2,3-f]quinolin-2-yl]methyl}amine or a pharmaceutically acceptable salt thereof.

14. A compound according to claim 1, wherein said compound is N-[(1R,3R)-3-(5-fluoro-1H-indol-3-yl)cyclopentyl]-N-{[(2S)-8-methyl-2,3-dihydro[1,4]dioxino[2,3-f]quinolin-2-yl]methyl}amine or a pharmaceutically acceptable salt thereof.

15. A compound according to claim 1, wherein said compound is N-[(1S,3S)-3-(5-fluoro-1H-indol-3-yl)cyclopentyl]-N-{[(2S)-8-methyl-2,3-dihydro[1,4]dioxino[2,3-f]quinolin-2-yl]methyl}amine or a pharmaceutically acceptable salt thereof.

16. A compound according to claim 1, wherein said compound is N-[(cis)-3-(5-fluoro-1H-indol-3-yl)cyclopentyl]-N-methyl-N-{[(2S)-8-methyl-2,3-dihydro[1,4]dioxino[2,3-f]quinolin-2-yl]methyl}amine or a pharmaceutically acceptable salt thereof.

17. A compound according to claim 1, wherein said compound is N-[(cis)-3-(5-fluoro-1-methyl-1H-indol-3-yl)cyclopentyl]-N-{[(2S)-8-methyl-2,3-dihydro[1,4]dioxino[2,3-f]quinolin-2-yl]methyl}amine or a pharmaceutically acceptable salt thereof.

18. A compound according to claim 1, wherein said compound is N-[(1R,3S)-3-(5-fluoro-1-methyl-1H-indol-3-yl)cyclopentyl]-N-{[(2S)-8-methyl-2,3-dihydro[1,4]dioxino[2,3-f]quinolin-2-yl]methyl}amine or a pharmaceutically acceptable salt thereof.

19. A compound according to claim 1, wherein said compound is N-[(1S,3R)-3-(5-fluoro-1-methyl-1H-indol-3-yl)cyclopentyl]-N-{[(2S)-8-methyl-2,3-dihydro[1,4]dioxino[2,3-f]quinolin-2-yl]methyl}amine or a pharmaceutically acceptable salt thereof.

20. A compound according to claim 1, wherein said compound is N-[(trans)-3-(5-fluoro-1-methyl-1H-indol-3-yl)cyclopentyl]-N-{[(2S)-8-methyl-2,3-dihydro[1,4]dioxino[2,3-f]quinolin-2-yl]methyl}amine or a pharmaceutically acceptable salt thereof.

21. A compound according to claim 1, wherein said compound is N-[(cis)-4-(5-fluoro-1H-indol-3-yl)cyclohexyl]-N-{[(2S)-8-methyl-2,3-dihydro[1,4]dioxino[2,3-f]quinolin-2-yl]methyl}amine or a pharmaceutically acceptable salt thereof.

22. A compound according to claim 1, wherein said compound is N-[(trans)-4-(5-fluoro-1H-indol-3-yl)cyclohexyl]-N-{[(2S)-8-methyl-2,3-dihydro[1,4]dioxino[2,3-f]quinolin-2-yl]methyl}amine or a pharmaceutically acceptable salt thereof.

23. A compound according to claim 1, wherein said compound is N-[(trans)-3-(5-Fluoro-1H-indol-3-yl)cyclopentyl]-N-{[(8S)-2-methyl-7,8-dihydro[1,4]dioxino[2,3-g][1,3]benzoxazol-8-yl]methyl}amine or a pharmaceutically acceptable salt thereof.

24. A compound according to claim 1, wherein said compound is N-[(cis)-3-(5-Fluoro-1H-indol-3-yl)cyclopentyl]-N-{[(8S)-2-methyl-7,8-dihydro[1,4]dioxino[2,3-g][1,3]benzoxazol-8-yl]methyl}amine or a pharmaceutically acceptable salt thereof.

25. A compound according to claim 1, wherein said compound is N-[(cis)-4-(5-fluoro-1H-indol-3-yl)cyclohexyl]-N-{[(8S)-2-methyl-7,8-dihydro[1,4]dioxino[2,3-g][1,3]benzoxazol-8-yl]methyl}amine; or a pharmaceutically acceptable salt thereof.

26. A compound according to claim 1, wherein said compound is N-[(1R*,3S*)-3-(5-fluoro-1H-indol-3-yl)cyclopentyl]-N-methyl-N-{[(2S)-8-methyl-2,3-dihydro[1,4]-dioxino[2,3-f]quinolin-2-yl]methyl}amine; or a pharmaceutically acceptable salt thereof.

27. A method of inhibiting serotonin reuptake in treating a subject suffering from a condition selected from depression, anxiety, panic disorder, post-traumatic stress disorder, premenstrual dysphoric disorder, attention deficit disorder, obsessive compulsive disorder, social anxiety disorder, generalized anxiety disorder, obesity, eating disorders, vasomotor flushing, cocaine and alcohol addiction, and sexual dysfunction, comprising the step of providing to said subject suffering from said condition, a therapeutically effective amount of a compound according to claim 1.

28. A method according to claim 27, wherein the condition is depression.

29. A method according to claim 27, wherein the condition is selected from the group consisting of obsessive compulsive disorder, panic attacks, generalized anxiety disorder, and social anxiety disorder.

30. A pharmaceutical composition, comprising:

an effective amount of compound according to claim 1 or pharmaceutically acceptable salt thereof; and a pharmaceutically acceptable carrier or excipient.

* * * * *